US012635958B1

(12) United States Patent
Dua et al.

(10) Patent No.: US 12,635,958 B1
(45) Date of Patent: May 26, 2026

(54) SYSTEM AND METHOD FOR BACKGROUND SENSING OF PERIPHERAL OXYGEN SATURATION

(71) Applicant: Apple Inc., Cupertino, CA (US)

(72) Inventors: Aditya Dua, Santa Cruz, CA (US); Dashiell R. Bodington, Palo Alto, CA (US); Christopher J. Brouse, Saratoga, CA (US); Sankalita Saha, Saratoga, CA (US); Mai Tuyet Le, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 311 days.

(21) Appl. No.: 17/472,536

(22) Filed: Sep. 10, 2021

Related U.S. Application Data

(60) Provisional application No. 63/077,292, filed on Sep. 11, 2020.

(51) Int. Cl.
*A61B 5/00* (2006.01)
*A61B 5/1455* (2006.01)

(52) U.S. Cl.
CPC ........ *A61B 5/7285* (2013.01); *A61B 5/14552* (2013.01); *A61B 5/721* (2013.01); *A61B 2562/0242* (2013.01)

(58) Field of Classification Search
CPC ... A61B 5/7285; A61B 5/14552; A61B 5/721; A61B 2562/0242
See application file for complete search history.

(56) References Cited

U.S. PATENT DOCUMENTS

| | | | | |
|---|---|---|---|---|
| 5,226,417 A | * | 7/1993 | Swedlow | A61B 5/721 |
| | | | | 356/41 |
| 9,442,523 B2 | | 9/2016 | Lee et al. | |
| 9,603,524 B2 | | 3/2017 | Park et al. | |
| 10,874,348 B1 | * | 12/2020 | Han | A61B 5/6843 |
| 2004/0034294 A1 | * | 2/2004 | Kimball | A61B 5/6826 |
| | | | | 600/323 |

(Continued)

OTHER PUBLICATIONS

Non-Final Office Action received for U.S. Appl. No. 17/472,537, mailed on Jun. 21, 2023, 18 pages.

(Continued)

*Primary Examiner* — Abid A Mustansir
(74) *Attorney, Agent, or Firm* — Kubota & Basol LLP

(57) ABSTRACT

A characteristic (e.g., SpO2) of a user's physiological signals can be estimated using background sensing with a pulse oximeter. For example, measurements by the optical sensor may be made when one or more criteria are satisfied that indicate conditions for a reliable SpO2 reading. In some examples, the measurements by the optical sensor can be spaced out in time. In some examples, a background measurement by the optical sensor can include multiple windows of data that can be processed, and the results of processing can be combined to determine the SpO2 estimate. In some examples, a background measurement can be terminated earlier and/or processing of some windows of data can be skipped when sufficient physiological signals have been collected to generate an estimate of SpO2 or when the conditions during the measurement(s) indicate that the physiological signals are unlikely to yield a reliable estimate of SpO2.

19 Claims, 16 Drawing Sheets

(56)  References Cited

U.S. PATENT DOCUMENTS

| | | | |
|---|---|---|---|
| 2008/0058773 A1 | 3/2008 | John | |
| 2008/0177194 A1 | 7/2008 | Zhang et al. | |
| 2012/0179011 A1 | 7/2012 | Moon et al. | |
| 2015/0164428 A1* | 6/2015 | Townsend | A61B 5/349 |
| | | | 702/69 |
| 2015/0289791 A1* | 10/2015 | Marcus | A61B 5/14552 |
| | | | 600/323 |
| 2016/0270708 A1* | 9/2016 | Tateda | A61B 5/7278 |
| 2017/0065178 A1 | 3/2017 | Suzuki et al. | |
| 2017/0095215 A1* | 4/2017 | Watson | A61B 5/0002 |
| 2017/0119315 A1 | 5/2017 | Leboeuf et al. | |
| 2017/0325698 A1* | 11/2017 | Allec | A61B 5/14552 |
| 2017/0325749 A1 | 11/2017 | Shah et al. | |
| 2017/0354326 A1 | 12/2017 | Pugh et al. | |
| 2018/0344181 A1 | 12/2018 | Schroeder et al. | |
| 2019/0038224 A1* | 2/2019 | Zhang | A61B 5/6843 |
| 2019/0130730 A1 | 5/2019 | Boyer | |
| 2020/0245883 A1 | 8/2020 | Lucci et al. | |
| 2020/0373019 A1 | 11/2020 | Hold et al. | |
| 2021/0251537 A9 | 8/2021 | Hu et al. | |

OTHER PUBLICATIONS

Final Office Action received for U.S. Appl. No. 17/472,537, mailed on Feb. 6, 2024, 20 pages.

* cited by examiner

PHOTOPLETHYSMOGRAPHY (PPG) SIGNAL

SYSTEM AND METHOD FOR BACKGROUND SENSING OF PERIPHERAL OXYGEN SATURATION

CROSS-REFERENCE TO RELATED APPLICATIONS

This application claims the benefit of U.S. Provisional Application No. 63/077,292, filed Sep. 11, 2020, the content of which is incorporated herein by reference in its entirety for all purposes.

FIELD OF THE DISCLOSURE

This relates generally to pulse oximetry systems and methods, and more particularly, to pulse oximetry systems and methods for background sensing of peripheral oxygen saturation.

BACKGROUND OF THE DISCLOSURE

Information or characteristics (e.g., pulse rate or arterial oxygen saturation) of a user's physiological signals can be determined by pulse oximetry systems and methods. In a basic form, pulse oximetry systems and methods can utilize one or more light emitters to illuminate a user's tissue and one or more light detectors to receive light that enters and probes a subsurface volume of tissue. The light emitters and light detectors can be in contact with the tissue or can be remote (i.e., not in contact) to the tissue surface. For example, arterial oxygen saturation can be estimated based on a perfusion index ratio for two different wavelengths of light. However, the estimates of information or characteristics of a user's physiological signals may be inaccurate when the light emitters or light detectors are not in good contact, the light emitters or detectors are oriented differently with respect to the tissue surface than expected, there are other anomalies in the path of light from light emitters to light detectors, or under other conditions that results in measurements that are incompatible with assumptions of pulse oximetry.

SUMMARY OF THE DISCLOSURE

This relates to systems and methods for background sensing of a characteristic of a user's physiological signals. For example, the physiological characteristic can be oxygen saturation of the hemoglobin in arterial blood (SaO2) as estimated by a pulse oximeter (peripheral oxygen saturation SpO2). In some examples, sensing of peripheral oxygen saturation may be performed opportunistically using optical sensor in the background without user intervention. The estimates of SpO2 can be used to monitor trends and/or provide notifications regarding SpO2 readings (e.g., if an SpO2 reading falls below a threshold). For example, measurements of physiological signals by the optical sensor may be made when one or more criteria are satisfied that indicate conditions for a reliable SpO2 reading (e.g., when the user is stationary, in a favorable posture, and/or not interacting with the device including the optical sensor). In some examples, to reduce power consumption and/or to estimate a user's SpO2 readings throughout the day, the measurements by the optical sensor can be spaced out in time. In some examples, a background measurement by the optical sensor can include multiple windows of data (e.g., physiological signals) that can be processed, and the results of processing can be combined to determine the SpO2 estimate. In some examples, a background measurement can be terminated earlier and/or processing of some of the windows of data can be skipped to save power when sufficient physiological signals (e.g., a threshold number of windows of data) have been collected to generate an estimate of SpO2 or when the conditions during the measurement(s) indicate that the physiological signals are unlikely to yield a reliable estimate of SpO2.

This also relates to systems and methods for background sensing of a characteristic of a user's physiological signals using different sampling rates. For example, the physiological characteristic can be oxygen saturation of the hemoglobin in arterial blood as estimated by a pulse oximeter. In some examples, sensing of peripheral oxygen saturation may be performed opportunistically using optical sensor in the background without user intervention. In some examples, the optical sensor can be configured to measure a first plurality of physiological signals at a first sampling rate in a first mode and can be configured to measure a second plurality of physiological signals at a second sampling rate, greater than the first sampling rate, in a second mode. The optical sensor can transition (or not transition) from the first mode to the second mode based on one or more first criteria (e.g., including a criterion that is satisfied when a first threshold number of the first plurality of SpO2 estimates falls below a first SpO2 estimate threshold without an intervening one of the first plurality of estimates exceeding a second SpO2 estimate threshold) and can transition (or not transition) from the second mode to the first mode based on one or more second criteria (e.g., termination criteria). In some examples, the systems can alert a user regarding a characteristic of a user's physiological signals using measurements for an optical sensor operating using one or multiple sampling rates. For example, a user can be alerted to sustained low SpO2 measurements based on opportunistic sensing using the optical sensor in the background without user intervention. The alert can be generated when one or more third criteria are satisfied. The one or more third criteria can include a criterion that is satisfied when a threshold number of SpO2 estimates have values below a threshold from measurement of the optical sensing in the first and/or in the second operating mode. In some examples, the measurements from the optical sensor operating at a higher sampling rate in the second mode can be used to confirm low oxygen saturation (e.g., when insufficient number of low oxygen saturation measurements are recorded at the first sampling rate). In some examples, the alert can include a notification (e.g., displayed on the display, can be stored on the device or transmitted to another device, or can be reported with other feedback mechanisms (e.g., audio feedback, visual feedback, haptic feedback, etc.)).

DETAILED DESCRIPTION

Figure 1A:
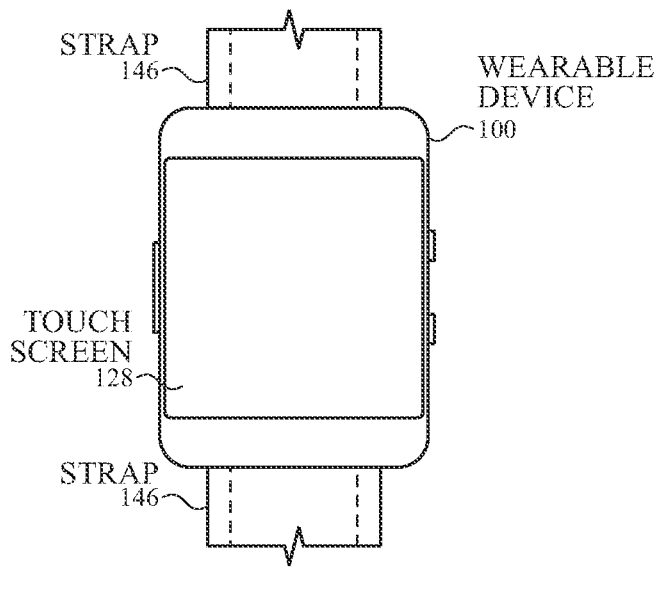
FIGS. 1A-1B illustrate views of an exemplary electronic device including one or more optical sensors according to examples of the disclosure.

In the following description of examples, reference is made to the accompanying drawings which form a part hereof, and in which it is shown by way of illustration specific examples that are optionally practiced. It is to be understood that other examples are optionally used and structural changes are optionally made without departing from the scope of the disclosed examples.

This relates to systems and methods for robust estimation of a physiological characteristic (e.g., arterial blood oxygen saturation) using a user's physiological signals. As used herein, physiological signals refer to signals generated by a physiological sensor (e.g., a photoplethysmogram (PPG) signal) that can be used for estimating the physiological characteristic (or condition) of a patient or user. A user's physiological signals can be determined by measurements using pulse oximetry systems. Such pulse oximetry systems can be designed to be sensitive to changes in the red blood cell number/concentration, volume, or blood oxygen state included in the sample or a user's vasculature. In a basic form, pulse oximetry systems can employ a light emitter (or plurality thereof) that injects light into the user's tissue and a light detector (or plurality thereof) to receive light that reflects and/or scatters and exits the tissue. In some examples, at least a portion of the photon path length interacts with tissue subsurface structures. Pulse oximetry systems can include, but are not limited to, arterial blood oxygen saturation estimation systems (SpO2 systems) configured to capture optical signals such as PPG signals. SpO2 systems can estimate a characteristic of physiological signals based on the attenuation of light (as measured by a physiological signal sensor) that varies over the duration of the cardiac cycle. Attenuation can be due to absorption, and/or scattering resulting from physiological/mechanical changes. Physiological/mechanical changes can include, but are not limited to, red blood cell number, cell/blood volume, red blood cell orientation, red blood cell/blood velocity, shear force, location/spatial distribution, concentration in the tissue, or other tissue properties (e.g., hydration, etc.), or a combination thereof. The estimated characteristics of the physiological signals (e.g., derive from the PPG signals) can include SpO2, heart rate, etc.

This also relates to systems and methods for background sensing of a characteristic of a user's physiological signals. For example, the physiological characteristic can be oxygen saturation of the hemoglobin in arterial blood (SaO2) as estimated by a pulse oximeter (peripheral oxygen saturation SpO2). In some examples, sensing of peripheral oxygen saturation may be performed opportunistically using optical sensor in the background without user intervention. The estimates of SpO2 can be used to monitor trends and/or provide notifications regarding SpO2 readings (e.g., if an SpO2 reading falls below a threshold). For example, measurements of physiological signals by the optical sensor may be made when one or more criteria are satisfied that indicate conditions for a reliable SpO2 reading (e.g., when the user is stationary, in a favorable posture, and/or not interacting with the device including the optical sensor, such as touching the touch screen). In some examples, to reduce power consumption and/or to estimate a user's SpO2 readings throughout the day, the measurements by the optical sensor can be spaced out in time. In some examples, a background measurement by the optical sensor can include multiple windows of data (e.g., physiological signals) that can be processed, and the results of processing can be combined to determine the SpO2 estimate. In some examples, a background measurement can be terminated earlier and/or processing of some of the windows of data can be skipped to save power when sufficient physiological signals (e.g., a threshold number of windows of data) have been collected to generate an estimate of SpO2 or when the conditions during the measurement(s) indicate that the physiological signals are unlikely to yield a reliable estimate of SpO2.

This also relates to systems and methods for background sensing of a characteristic of a user's physiological signals using different sampling rates. For example, the physiological characteristic can be oxygen saturation of the hemoglobin in arterial blood (SaO2) as estimated by a pulse oximeter (peripheral oxygen saturation SpO2). In some examples, sensing of peripheral oxygen saturation may be performed opportunistically using optical sensor in the background without user intervention. In some examples, the optical sensor can be configured to measure a first plurality of physiological signals at a first sampling rate in a first mode and can be configured to measure a second plurality of physiological signals at a second sampling rate, greater than the first sampling rate, in a second mode. The optical sensor can transition (or not transition) from the first mode to the second mode based on one or more first criteria (e.g., including a criterion that is satisfied when a first threshold number of the first plurality of SpO2 estimates falls below a first SpO2 estimate threshold without an intervening one of the first plurality of estimates exceeding a second SpO2 estimate threshold) and can transition (or not transition) from the second mode to the first mode based on one or more second criteria (e.g., termination criteria). In some examples, the systems can alert a user regarding a characteristic of a user's physiological signals using measurements for an optical sensor operating using one or multiple sampling rates. For example, a user can be alerted to sustained low SpO2 measurements based on opportunistic sensing using the optical sensor in the background without user intervention. The alert can be generated when one or more third criteria are satisfied. The one or more third criteria can include a criterion that is satisfied when a threshold number of SpO2 estimates have values below a threshold from measurement of the optical sensing in the first and/or in the second operating mode. In some examples, the measurements from the optical sensor operating at a higher sampling rate in the second mode can be used to confirm low oxygen saturation (e.g., when insufficient number of low oxygen saturation measurements are recorded at the first sampling rate). In some examples, the alert can include a notification (e.g., displayed on the display, can be stored on the device or transmitted to another device, or can be reported with other feedback mechanisms (e.g., audio feedback, visual feedback, haptic feedback, etc.)).

Figure 1C:
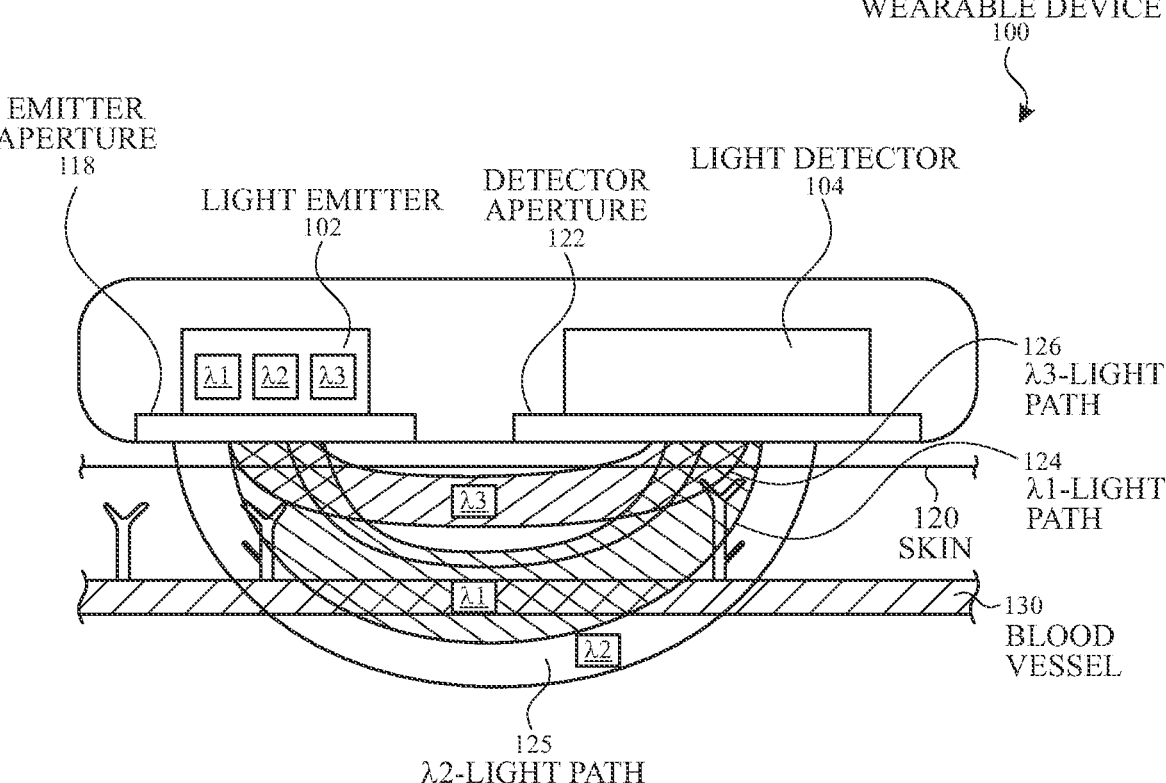
FIG. 1C illustrates a cross-sectional view of exemplary wearable device including one or more light emitters and one or more light detectors according to examples of the disclosure.
Figure 1B:
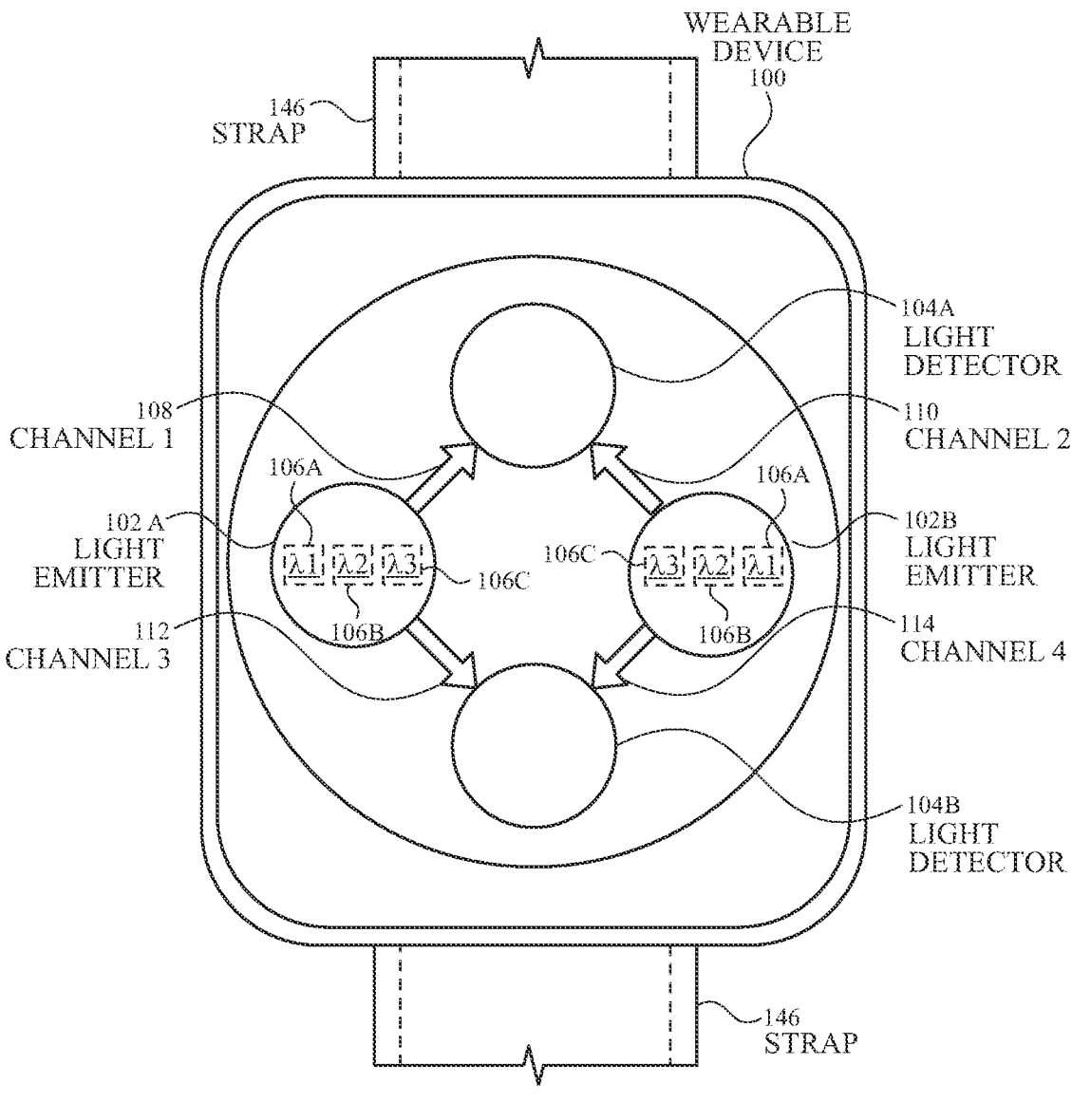

FIGS. 1A-1B illustrate views of an exemplary electronic device including one or more optical sensors according to examples of the disclosure. FIG. 1A illustrates a top view of an exemplary wearable device 100 that can include a touch screen 128 and can be attached to a user using a strap 146 or other fastener. FIG. 1B illustrates a bottom view (underside) of exemplary wearable device 100 including one or more optical sensors comprising one or more light emitters and one or more light detectors according to examples of the disclosure. For example, FIG. 1B illustrates device 100 that can include light emitters 102A-102B and light detectors 104A-104B. Device 100 can be positioned such that light emitters 102A-102B and light detectors 104A-104B are proximate to a user's skin or any other tissue site. For example, device 100 can be held in the user's hand or strapped to the user's wrist, among other possibilities. In some examples, light emitters 102A-102B and light detectors 104A-104B can be in close proximity (e.g., within a threshold distance, such as 5 mm, for example) to the surface of user's skin or can be physically contacting a surface of user's skin, which can reduce the amount of detected light that has not traveled through tissue.

As described herein, each light emitter represents a unique location on the device at which light can be emitted from device, and each light detector represents a unique location on the device at which the device can collect light. The light emitters and light detectors can preferably be optically isolated within the device such that emitted light from an emitter exits the device before being sensed by a detector. As described herein, light emitters can be configured to emit light at a plurality of wavelengths (e.g., at least two wavelengths for SpO2 measurements).

In some examples, each of light emitters 102A-102B can include one or more light emitting components to generate light at different wavelengths. For example, FIG. 1B illustrates each light emitter 102A-102B including three discrete light emitting components 106A-106C (e.g., light emitting diodes (LEDs) or organic light emitting diodes (OLEDs)) configured to generate light at multiple wavelengths including at least wavelengths λ1, λ2, and λ3, respectively. Although three wavelengths are shown, in some examples, device 100 may include light emitting components at fewer or more wavelengths (e.g., at λ1 and λ2 for pulse oximetry). Additionally, in some examples, each light emitter can include one light emitting component with a tunable wavelength (e.g., voltage or current controlled) or with different filters, rather than using a different light emitting component for each wavelength. In some examples, each light emitter 102A-102B can be optically coupled to each light detector 104A-104B for each wavelength. For example, light emitter 102A can be optically coupled to both light detectors 104A-

104B and light emitter 102B can be optically coupled to both light detectors 104A-104B. Light emitter 102A can be configured to emit light (at one or more wavelengths) detected by light detector 104A and detected by light detector 104B. Light emitter 102B can also be configured to emit light (at one or more wavelengths) detected by light detector 104A and detected by light detector 104B. As illustrated in FIG. 1B, a first channel 108 can be used to measure signal at light detector 104A from light emitter 102A (at each respective wavelength), a second channel 110 can be used to measure signal at light detector 104A from light emitter 102B (at each respective wavelength), a third channel 112 can be used to measure signal at light detector 104B from light emitter 102A (at each respective wavelength), and a fourth channel 114 can be used to measure signal at light detector 104B from light emitter 102B (at each respective wavelength). The measured signal at each detector can include light measured from various light paths (e.g., expected distributions of possible light paths through the skin and/or air) between the respective emitter and detector of the channel.

Device 100 can also include processing circuitry to process light detected from light detectors 104A-104B. In some examples, the processing circuitry can be used to determine the user's physiological signals and extract information (e.g., one or more characteristics) from the physiological signals. In some examples, a physiological characteristic can be one or more measures of heart rate or a hemoglobin oxygen saturation level (e.g., an arterial oxygen saturation (SpO2)). In some examples, the processing circuitry can remove or reduce motion artifacts from the physiological signals to account for non-cardiac-induced pulsatile blood volume changes. In some examples, the processing circuitry can process light detected from light detectors 104A-104B for functions independent from determining the user's physiological signals.

FIG. 1C illustrates a cross-sectional view of exemplary wearable device 100 including one or more light emitters and one or more light detectors according to examples of the disclosure. As illustrated in FIG. 1C, light emitter 102 can generate light at one or more wavelengths that can exit device 100 at emitter aperture 118 (e.g., a window). The light can be directed towards, and incident upon, the user's skin 120 and some of the light can be returned back toward device 100 (e.g., reflected and/or scattered from interacting with the skin). The light can reenter device through detector aperture 122 (e.g., a window) and be detected by light detector 104. A portion of light can be absorbed by molecules in skin 120, vasculature, and/or blood. Pulsatile blood flow in the user can lead to changes in the arterial vessel diameters, tissue hemoglobin concentration or volume, red blood cell orientation, velocity, or other physical states during a pressure change (e.g., diastole to systole), which can be included in light (e.g., via a scattering or absorption contrast mechanism) within the field of view of light detector 104. In some examples, heart rate can be estimated based on the changes in the detected light at one or more wavelengths due to pulsatile blood flow. In some examples, oxygen saturation in the blood can be estimated based on a ratio between physiological signal measurements (e.g., light intensity signals at light detectors) at two (or more) wavelengths. For example, oxygen saturation can be estimated based on a relative modulation ratio at two or more wavelengths. In some examples, the modulation ratio can be a perfusion index (PI) ratio based on physiological signal measurements at two or more wavelengths. Although the intensity of the physiological signal (or more generally the magnitude of each independent wavelength measurement) may change due to variations in the pulsations of blood, movement and the heterogeneity of tissue, the relative modulation ratio (e.g., between red light and infrared light) can be relatively stable indicator of oxygen saturation (e.g., via an empirical mapping between the relative modulation ratio and oxygen saturation).

In some examples, the signals from the one or more light emitters and one or more light detectors can be utilized to perform other functions aside from measuring the user's physiological signals and extracting information/characteristics from the physiological signals. For example, one or more light emitters and one or more light detectors can be configured for monitoring whether or not the device remains in contact with a user's skin (e.g., on-wrist and/or off-wrist detection) and/or whether the device is in contact with a non-skin surface such as a table.

FIG. 1C illustrates exemplary light paths for three different wavelengths λ1, λ2 and λ3. Light path 124 can correspond to expected distributions of possible light paths at wavelength λ1 (e.g., in the wavelength range of 620 nm-750 nm) and light path 125 can correspond to expected distributions of possible light paths at wavelength λ2 (e.g., in the wavelength range of 750 nm-1400 nm). In some examples, wavelength λ1 can be in the range of visible light (e.g., 400 nm-700 nm) and wavelength λ2 can be in the range of near-infrared (NIR) light (e.g., 700-1100 nm), which can be strongly absorbed by blood and other molecules in the user's tissue and blood. In some examples, wavelength λ1 can be red light and wavelength λ2 can be IR light. Light path 126 can correspond to expected distributions of possible light paths at wavelength λ3 (e.g., in the wavelength range of 495 nm-570 nm). In some examples, λ3 can be in a lower wavelength range of visible light (e.g., 400 nm-495 nm), such as blue light, or near ultraviolet light (e.g., 300 nm-400 nm), or other portions of the visible light, NIR, short-wave IR spectra. It should be understood that these wavelength ranges are for exemplary purposes and different wavelength ranges are possible for 21, 22, and 23 (or any additional wavelengths). In some examples, the light at multiple wavelengths from the multiple light emitting components of an emitter exiting the device can preferably partially or fully overlap (e.g., light paths 124-126 can be partially or fully overlapping). As shown in FIG. 1C, in some examples, different wavelengths can penetrate different depths within skin 120. For example, light paths 124 and 125 corresponding to wavelengths λ1 and λ2 can penetrate more deeply within the skin 120 and underlying tissue, whereas light path 126 corresponding to wavelength λ3 can penetrate less deeply within skin 120 and the underlying tissue. Additionally, although the light paths may penetrate different depths, it is understood that light at some wavelengths can penetrate a variety of depths including shallower and deeper within the tissue.

Skin 120 and underlying tissue can include the blood vessels (arterial and venous) such as blood vessel 130. Light emitter 102 and light sensor 104 can be located and wavelengths can be selected such that light paths 124 and 125 corresponding to wavelengths λ1 and λ2 can be sensitive to arterial blood volume changes to enable an estimation of the characteristic of a user's physiological signals.

Figure 1D:
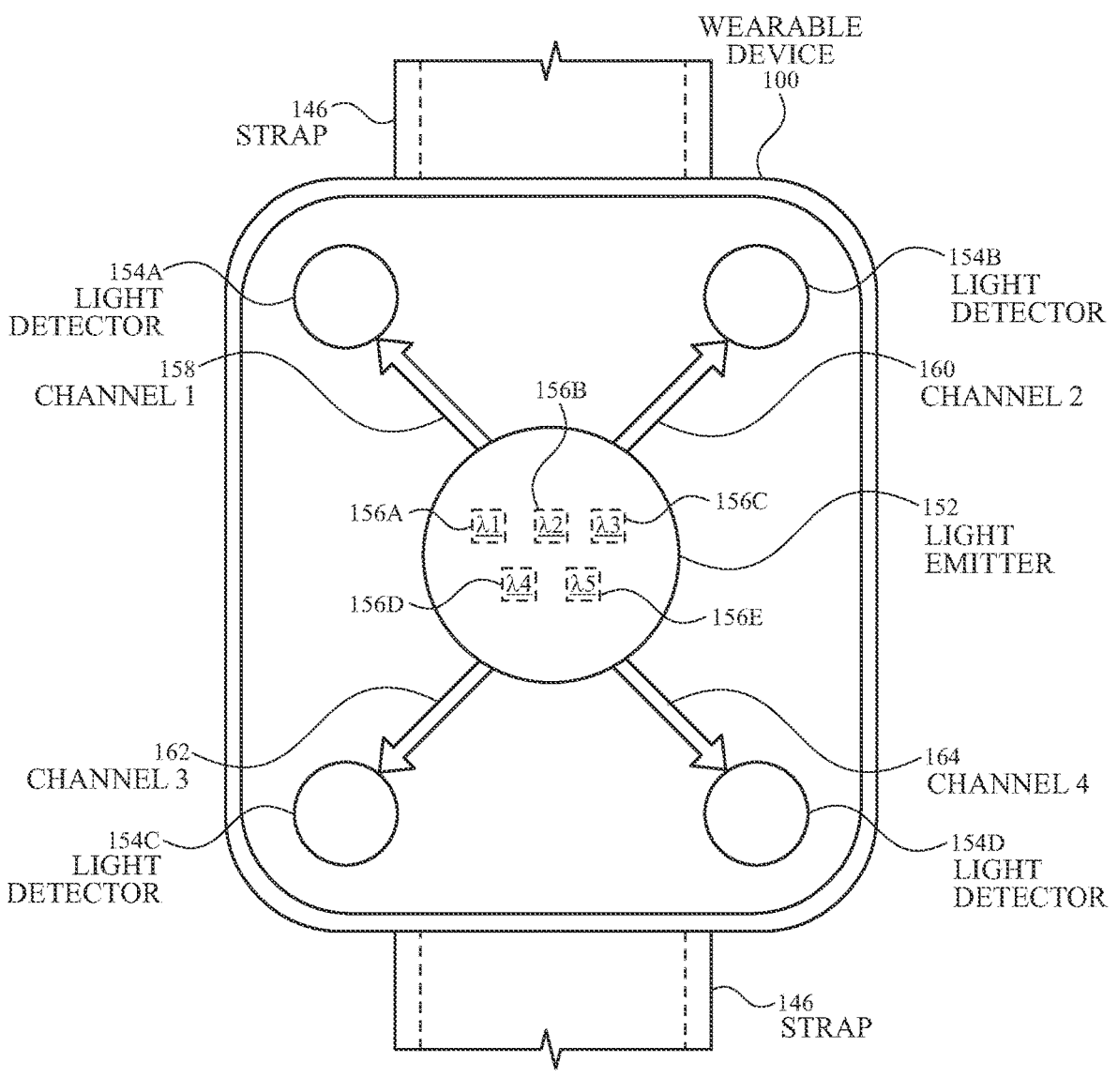
FIGS. 1D-1E illustrate alternative arrangements of light emitters and light detectors on the underside of an exemplary electronic device according to examples of the disclosure.
Figure 1E:
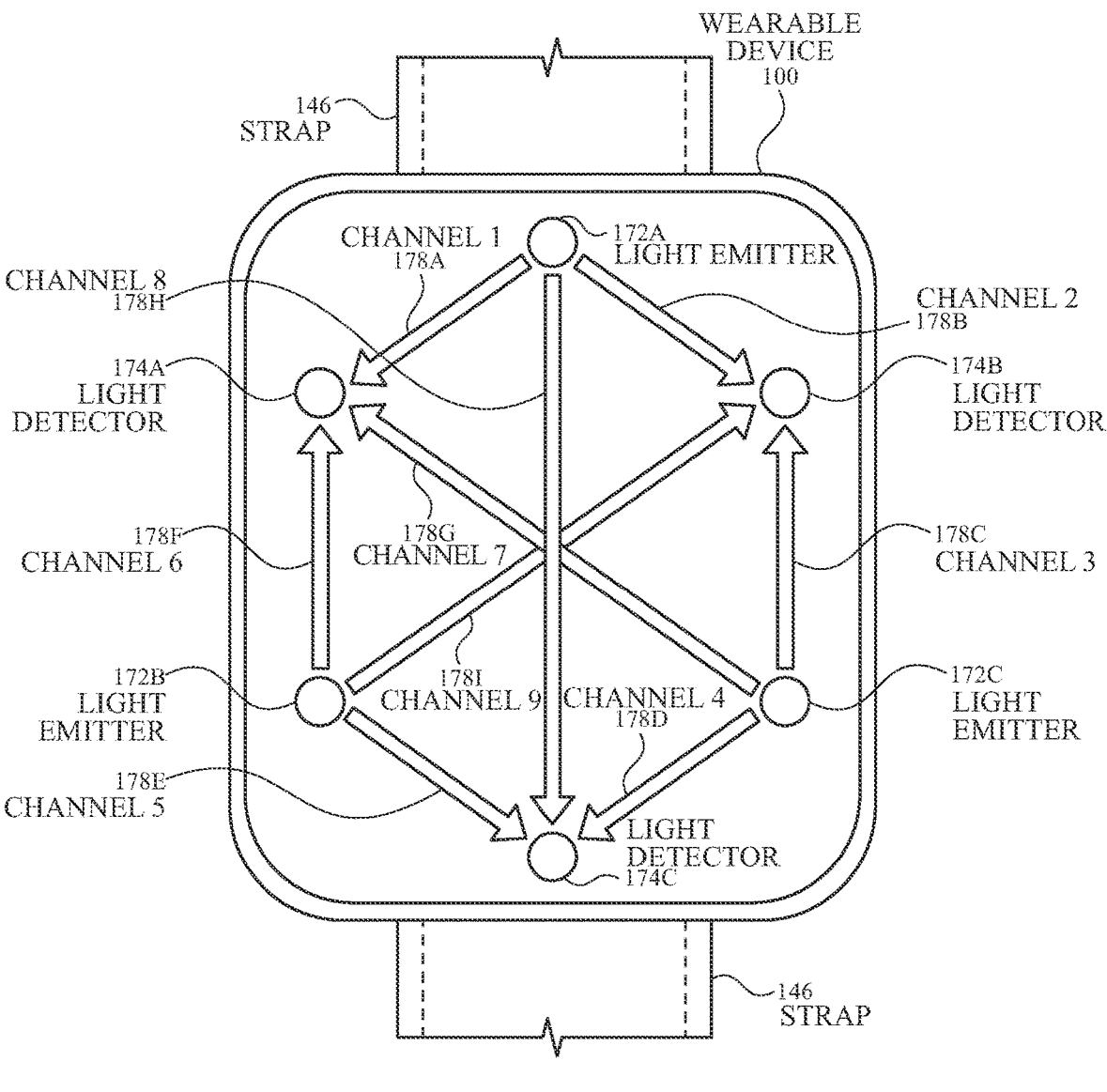

FIGS. 1D-1E illustrate alternative arrangements of light emitters and light detectors on the underside of an exemplary electronic device according to examples of the disclosure. FIG. 1D illustrates device 100 that can include light emitter 152 in a center of the device and light detectors 154A-154D. Light emitter 152 can include one or more light emitting components to generate light at different wavelengths. For example, FIG. 1D illustrates light emitter 152 including five light emitting components 156A-E (e.g., LEDs or OLEDs) configured to generate light at wavelengths λ1, λ2, λ3, λ4 and λ5, respectively. Although five wavelengths are shown, in some examples, device 100 may include light emitting components at fewer or more wavelengths (or one tunable/filterable light emitting component) or may include different types of light emitting components (e.g., laser diodes). Light emitter 152 can be optically coupled to one or more (or each of) light detectors 154A-154D for one or more (or each of the) wavelengths. In some examples, light emitter 152 can be configured to emit light (at one or more wavelengths) detected by light detector 154A, detected by light detector 154B, detected by light detector 154C and detected by light detector 154D. As illustrated in FIG. 1D, a first channel 158 can be used to measure signal at light detector 154A from light emitter 152 (e.g., at each respective wavelength), a second channel 160 can be used to measure signal at light detector 154B from light emitter 152 (at each respective wavelength), a third channel 162 can be used to measure signal at light detector 154C from light emitter 152 (at each respective wavelength), and a fourth channel 164 can be used to measure signal at light detector 154D from light emitter 152 (at each respective wavelength). The measured signal at each detector (at each respective wavelength) can include light that has traversed various light paths (e.g., expected distributions of possible light paths through the skin and/or air) between the respective emitter and detector of the channel.

Although FIGS. 1B and 1D illustrate four channels (each operable for emitting/detecting light at multiple wavelengths), in some examples, fewer or additional channels may be implemented. For example, a single channel including one light emitter and one light detector can be used. In some examples, additional light emitters and/or light detectors may be used to form additional channels. For example, adding one or more additional light detectors to the configurations in FIG. 1B or 1D can increase the number of channels.

FIG. 1E illustrates device 100 that can include multiple light emitters 172A-172C and multiple light detectors 174A-174C arranged in a pattern around the perimeter of the device. Although the three emitters and detectors are shown in a hexagonal arrangement with an alternating pattern of emitters/detectors, it is understood that other arrangements are possible with different shaped arrangements (e.g., circle, polygon, etc.), non-alternating arrangements, and/or using more or fewer light emitters and light detectors. Light emitter 172A-172C can include one or more light emitting components (not shown) to generate light at different wavelengths (e.g., λ1, λ2, λ3, etc.). Light emitters 172A-172C can be optically coupled to one or more (or each of) light detectors 174A-174C for one or more (or each of the) wavelengths. In some examples, light emitter 172A can be configured to emit light (at one or more wavelengths) detected by light detector 174A, detected by light detector 174B, and detected by light detector 174C. As illustrated in FIG. 1E, a first channel 178A can be used to measure signal at light detector 174A from light emitter 172A (e.g., at each respective wavelength), a second channel 178B can be used to measure signal at light detector 174B from light emitter 172A (at each respective wavelength), and a third channel 178H can be used to measure signal at light detector 174C from light emitter 172A (at each respective wavelength). In a similar manner, a fourth channel 178F can be used to measure signal at light detector 174A from light emitter 172B (e.g., at each respective wavelength), a fifth channel 178I can be used to measure signal at light detector 174B from light emitter 172B (at each respective wavelength), a sixth channel 178E can be used to measure signal at light detector 174C from light emitter 172B (at each respective wavelength), a seventh channel 178G can be used to measure signal at light detector 174A from light emitter 172C (e.g., at each respective wavelength), an eighth channel 178C can be used to measure signal at light detector 174B from light emitter 172C (at each respective wavelength), and a ninth channel 178D can be used to measure signal at light detector 174C from light emitter 172C (at each respective wavelength). The measured signal at each detector (at each respective wavelength) can include light that has traversed various light paths (e.g., expected distributions of possible light paths through the skin and/or air) between the respective emitter and detector of the channel.

It is understood that the light detectors of device 100 (e.g., light detector(s) 104, 104A-104B, 154A-154D, and 174A-174C) can, in some examples, include a single light detection component (e.g., photodiode or other suitable photodetector). In some examples, some or all of the light detectors of device 100 can include multiple light detection components (e.g., an array of photodiodes. Using multiple light detection components per light detector can allow for greater granularity in signal processing. Additionally or alternatively, the multiple light components can be used with different optical filters to provide simultaneous measurements for multiple wavelengths (e.g., each light detection component can include a different filter to enable measurement of a different wavelength of light).

Figure 2:
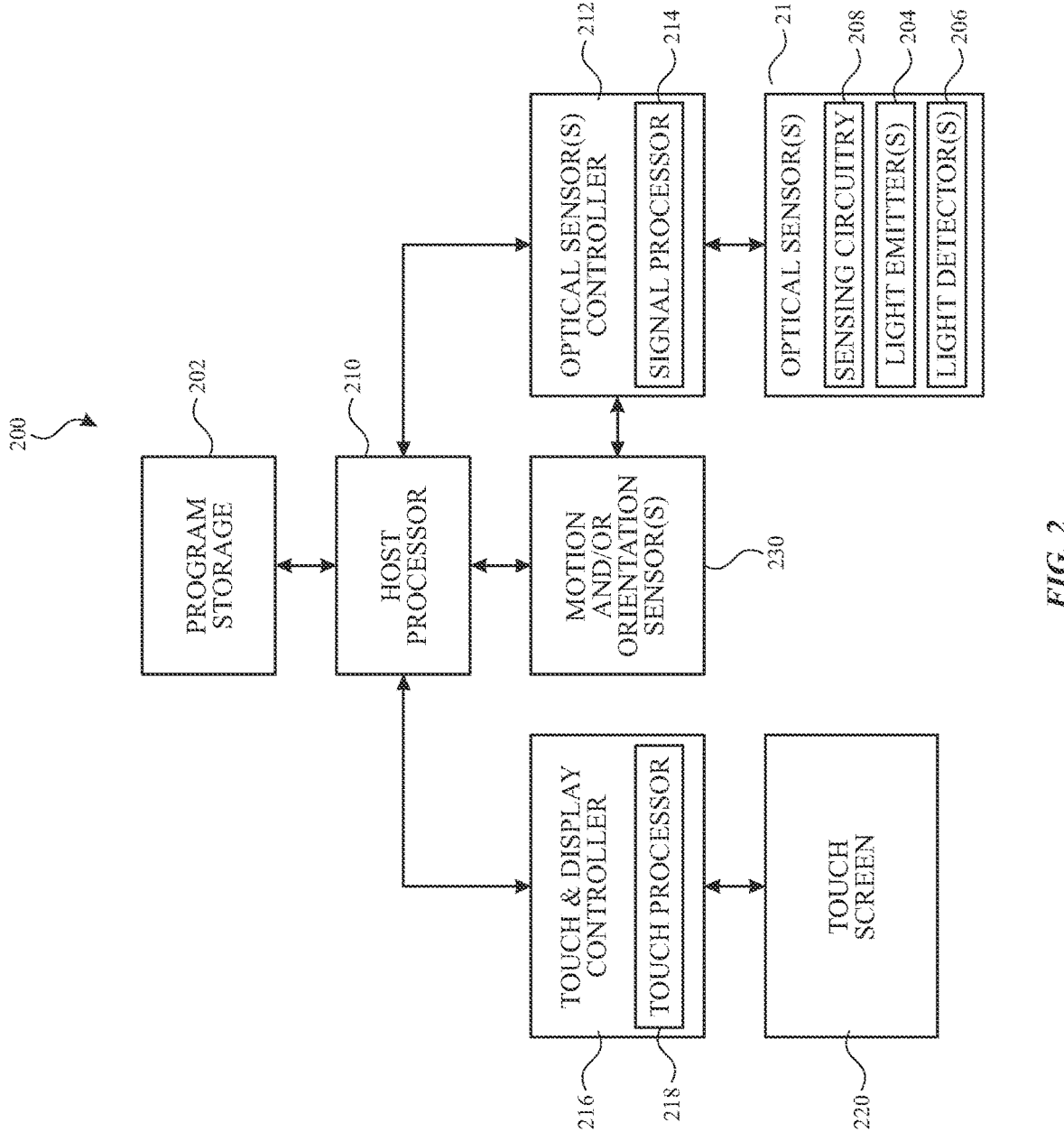
FIG. 2 illustrates an exemplary block diagram of a computing system including an optical sensor according to examples of the disclosure.

FIG. 2 illustrates an exemplary block diagram of a computing system including an optical sensor according to examples of the disclosure. Although primarily described herein as a wearable device, the computing system may alternatively be implemented partially or fully in a non-wearable device. For example, the sensors and/or processing described herein can be implemented partially or fully in a mobile telephone, media player, tablet computer, personal computer, server, etc. In some examples, the light emitters and light detectors can be implemented in a wearable device (e.g., a wristwatch) and the processing of the data can be performed in a non-wearable device (e.g., a mobile phone). Processing and/or storage of the physiological signals in a separate device can enable the device including the physiological sensors (e.g., a wristwatch) to be space and power efficient (which can be important features for portable/wearable devices).

Computing system 200 can correspond to device 100 illustrated in FIGS. 1A-1E (or may be implemented in other wearable or non-wearable electronic devices). Computing system 200 can include a processor 210 (or more than one processor) programmed to (configured to) execute instructions and to carry out operations associated with computing system 200. For example, using instructions retrieved from program storage 202, processor 210 can control the reception and manipulation of input and output data between components of computing system 200. Processor 210 can be a single-chip processor (e.g., an application specific integrated circuit) or can be implemented with multiple components/circuits.

In some examples, processor 210 together with an operating system can operate to execute computer code, and produce and/or use data. The computer code and data can reside within a program storage 202 that can be operatively coupled to processor 210. Program storage 202 can generally provide a place to hold data that is being used by computing system 200. Program storage block 202 can be any non-transitory computer-readable storage medium, and can store, for example, history and/or pattern data relating to PPG signals and relative modulation ratio (e.g., perfusion index ratio) values measured by a configuration of light emitter(s) 204 and light detector(s) 206 (e.g., as illustrated in FIG. 1B, 1D or 1E). By way of example, program storage 202 can include Read-Only Memory (ROM), Random-Access Memory (RAM), hard disk drive and/or the like. The computer code and data could also reside on a removable storage medium and loaded or installed onto computing system 200 when needed. Removable storage mediums include, for example, CD-ROM, DVD-ROM, Universal Serial Bus (USB), Secure Digital (SD), Compact Flash (CF), Memory Stick, Multi-Media Card (MMC) and/or a network component.

Computing system 200 can also include one or more input/output (I/O) controllers that can be operatively coupled to processor 210. I/O controllers can be configured to control interactions with one or more I/O devices (e.g., touch sensor panels, display screens, touch screens, physical buttons, dials, slider switches, joysticks, or keyboards). I/O controllers can operate by exchanging data between processor 210 and the I/O devices that desire to communicate with processor 210. The I/O devices and I/O controller can communicate through a data link. The data link can be a unidirectional or bidirectional link. In some cases, I/O devices can be connected to I/O controllers through wireless connections. A data link can, for example, correspond any wired or wireless connection including, but not limited to, PS/2, Universal Serial Bus (USB), Firewire, Thunderbolt, Wireless Direct, IR, RF, Wi-Fi, Bluetooth or the like.

For example, computing system 200 can include an optical sensor controller 212 operatively coupled to processor 210 and to one or more optical sensors 211. The optical sensor(s) can include light emitter(s) 204, light detector(s) 206 and corresponding sensing circuitry 208 (e.g., analog circuitry to drive emitters and measure signals at the detector, provide processing (e.g., amplification, filtering), and convert analog signals to digital signals). As described herein, light emitters 204 and light detectors 206 can be configured to generate and emit light into a user's skin and detect returning light (e.g., reflected and/or scattered) to measure a physiological signal (e.g., a PPG signal). The absorption and/or return of light at different wavelengths can also be used to determine a characteristic of the user (e.g., oxygen saturation, heart rate) and/or about the contact condition between the light emitters 204/light detectors 206 and the user's skin. Measured raw data from the light emitters 204, light detectors 206 and sensing circuitry 208 can be transferred to processor 210, and processor 210 can perform the signal processing described herein to estimate a characteristic (e.g., oxygen saturation, heart rate, etc.) of the user from the physiological signals. Processor 210 and/or optical sensor controller 212 can operate light emitters 204, light detectors 206 and/or sensing circuitry 208 to measure data from the optical sensor. In some examples, optical sensor controller 212 can include timing generation for light emitters 204, light detectors 206 and/or sensing circuitry 208 to sample, filter and/or convert (from analog to digital) signals measured from light at different wavelengths. Optical sensor controller 212 can process the data in signal processor 214 and report outputs (e.g., PPG signal, relative modulation ratio, perfusion index, heart rate, on-wrist/off-wrist state, etc.) to the processor 210. Signal processor 214 can be a digital signal processing circuit such as a digital signal processor (DSP). The analog data measured by the optical sensor(s) 211 can be converted into digital data by an analog to digital converter (ADC), and the digital data from the physiological signals can be stored for processing in a buffer (e.g., a FIFO) or other volatile or non-volatile memory (not shown) in optical sensor controller 212. In some examples, some light emitters and/or light detectors can be activated, while other light emitters and/or light detectors can be deactivated to conserve power, for example, or for time-multiplexing (e.g., to avoid interference between channels). In some examples, processor 210 and/or optical sensor controller 212 can store the raw data and/or processed information in memory (e.g., ROM or RAM) for historical tracking or for future diagnostic purposes. Additional detail regarding optical sensors and processing optical signals is described below.

Computing system 200 can also include one or more motion and/or orientation sensors 230, such as an accelerometer, a gyroscope, an inertia-measurement unit (IMU), etc. In some examples, the motion and/or orientation sensors 230 can include a multi-channel accelerometer (e.g., a 3-axis accelerometer).

Computing system 200 can also include, in some examples, a touch and display controller 216 operatively coupled to processor 210 and to touch screen 220. Touch screen 220 can be configured to display visual output in a graphical user interface (GUI), for example. The visual output can include text, graphics, video, and any combination thereof. In some examples, the visual output can include a text or graphical representation of the physiological signal (e.g., a PPG waveform) or a characteristic of the physiological signal (e.g., oxygen saturation, heart rate, etc.) Touch screen can be any type of display including a liquid crystal display (LCD), a light emitting polymer display (LPD), an electroluminescent display (ELD), a field emission display (FED), a light emitting diode (LED) display, an organic light emitting diode (OLED) display, or the like. Processor 210 can send raw display data to touch and display controller 216, and touch and display controller 216 can send signals to touch screen 220. Data can include voltage levels for a plurality of display pixels in touch screen 220 to project an image. In some examples, processor 210 can be configured to process the raw data and send the signals to touch screen 220 directly. Touch and display controller 216 can also detect and track touches or near touches (and any movement or release of the touch) on touch screen 220. For example, touch processor 218 can process data representative of touch or near touches on touch screen 220 (e.g., location and magnitude) and identify touch or proximity gestures (e.g., tap, double tap, swipe, pinch, reverse-pinch, etc.). Processor 210 can convert the detected touch input/gestures into interaction with graphical objects, such as one or more user-interface objects, displayed on touch screen 220 or perform other functions (e.g., to initiate a wake of the device or power on one or more components).

In some examples, touch and display controller 216 can be configured to send raw touch data to processor 210, and processor 210 can process the raw touch data. In some examples, touch and display controller 216 can process raw touch data itself (e.g., in touch processor 218). The processed touch data (touch input) can be transferred from touch processor 218 to processor 210 to perform the function corresponding to the touch input. In some examples, a separate touch sensor panel and display screen can be used, rather than a touch screen, with corresponding touch controller and display controller.

In some examples, the touch sensing of touch screen 220 can be provided by capacitive touch sensing circuitry (e.g., based on mutual capacitance and/or self-capacitance). For example, touch screen 220 can include touch electrodes arranged as a matrix of small, individual plates of conductive material or as drive lines and sense lines, or in another pattern. The electrodes can be formed from a transparent conductive medium such as ITO or ATO, although other partially or fully transparent and non-transparent materials (e.g., copper) can also be used. In some examples, the electrodes can be formed from other materials including conductive polymers, metal mesh, graphene, nanowires (e.g., silver nanowires) or nanotubes (e.g., carbon nanotubes). The electrodes can be configurable for mutual capacitance or self-capacitance sensing or a combination of mutual and self-capacitance sensing. For example, in one mode of operation, electrodes can be configured to sense mutual capacitance between electrodes; in a different mode of operation, electrodes can be configured to sense self-capacitance of electrodes. During self-capacitance operation, a touch electrode can be stimulated with an AC waveform, and the self-capacitance to ground of the touch electrode can be measured. As an object approaches the touch electrode, the self-capacitance to ground of the touch electrode can change (e.g., increase). This change in the self-capacitance of the touch electrode can be detected and measured by the touch sensing system to determine the positions of one or more objects when they touch, or come in proximity to without touching, the touch screen. During mutual capacitance operation, a first touch electrode can be stimulated with an AC waveform, and the mutual capacitance between the first touch electrode and a second touch electrode can be measured. As an object approaches the overlapping or adjacent region of the first and second touch electrodes, the mutual capacitance therebetween can change (e.g., decrease). This change in the mutual capacitance can be detected and measured by the touch sensing system to determine the positions of one or more objects when they touch, or come in proximity to without touching, the touch screen. In some examples, some of the electrodes can be configured to sense mutual capacitance therebetween and some of the electrodes can be configured to sense self-capacitance thereof.

Note that one or more of the functions described herein, including estimating a physiological characteristic according to examples of the disclosure, can be performed by firmware stored in memory (or in program storage 202) and executed by physiological sensor controller 212, touch and display controller 216 or processor 210. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, USB memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Referring back to FIG. 1B, light emitters 102A-102B can generate light and light detectors 104A-104B can measure light at multiple wavelengths (e.g., λ1, λ2, λ3). In some examples, three light emitting components 106A-106C can be co-located (within a threshold distance of one another, e.g., less than 5 mm) in each of light emitters 102A-102B. In some examples, each of the light emitting components can be driven in a time-multiplexed manner. For example, during a measurement period of duration T (from time t0 to t6), a first light emitting component 106A of light emitter 102A can be driven at wavelength λ1 and light can be detected at light detectors 104A-104B (from t0 to t1), a second light emitting component 106B of light emitter 102A can be driven at wavelength λ2 and light can be detected at light detectors 104A-104B (from t1 to t2), a third light emitting component 106C of light emitter 102A can be driven at wavelength λ3 and light can be detected at light detectors 104A-104B (from t2 to t3), a fourth light emitting component 106A of light emitter 102B can be driven at wavelength λ1 and light can be detected at light detectors 104A-104B (from t3 to t4), a fifth light emitting component 106B of light emitter 102B can be driven at wavelength λ2 and light can be detected at light detectors 104A-104B (from t4 to t5), and a sixth light emitting component 106C of light emitter 102B can be driven at wavelength λ3 and light can be detected at light detectors 104A-104B (from t5 to t6). Ideally, the measurement period can be less than a threshold duration. Reducing the duration of measurement period can allow for the measurements at different wavelengths to be as co-located in time as possible. In some examples, the duration of the measurement period can be less than 100 ms. The above measurements can result in a sample for each channel (e.g., four channels of FIG. 1B, 9 channels for FIG. 1E) at each wavelength (e.g., λ1, λ2, λ3) for the measurement period. The sample for each channel can be used to compute physiological characteristics such as perfusion indices, perfusion index ratios, SpO2, etc. In some examples, the light emitting components can be frequency-multiplexed such that multiple light emitting components to concurrently emit light and detectors can differentiate between the light emitting components based on the frequency content.

Figure 3A:
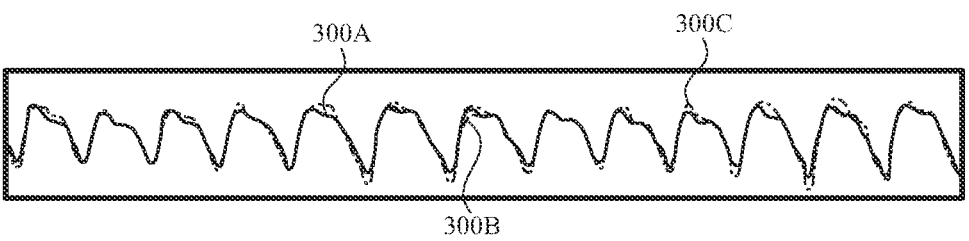
FIGS. 3A-3B illustrate example photoplethysmogram (PPG) signals measured at different wavelengths according to examples of the disclosure.
Figure 3B:
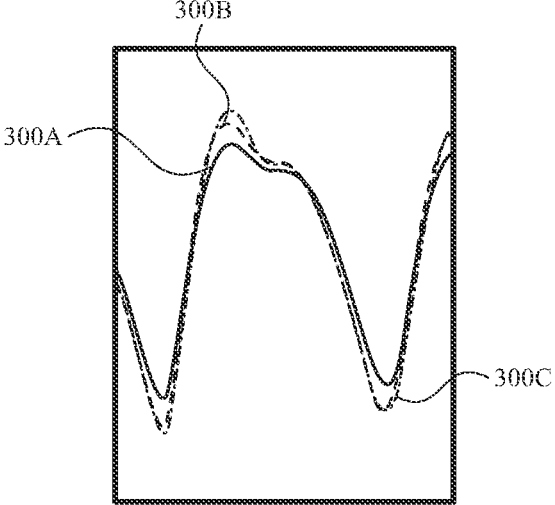

FIGS. 3A-3B illustrate example photoplethysmogram (PPG) signals measured at different wavelengths according to examples of the disclosure. The PPG signals can include cyclical "beats" (or "pulses") corresponding to a heartbeat (e.g., each "beat" or "pulse" indicative of one occurrence of the repeating cardiac cycle). FIGS. 3A-3B illustrate a PPG signal for each of wavelengths λ1, λ2 and λ3 (e.g., while device 100 is properly secured to skin 120 to establish good contact between the optical sensor(s) and the skin). FIG. 3A illustrates PPG signals 300A, 300B, 300C with multiple beats and FIG. 3B illustrates a larger view of an exemplary beat, in which the waveform shapes of PPG signals 300A-300C can be similar and correspond to pulsatile blood information. Although not shown in FIGS. 3A-3B, in some examples, when device is not properly secured to skin 120 (light or poor content), the waveform of PPG signal can be different in shape and/or relative amplitude (and may or may not correspond to pulsatile blood information) for wavelength λ3 (e.g., different than the shape and/or relative amplitude of PPG signal 300C, whereas the waveforms of PPG signals 300A and 300B may be similar even with poorer contact between the optical sensor and tissue). As a result, poor contact conditions may result in an inaccurate estimate of the physiological signal characteristic.

In some examples, a sensor can be used to estimate a contact condition. For example, device 100 can include a touch sensor (e.g., capacitive, resistive, ultrasonic, etc.), proximity sensor (e.g., an infrared sensor), force sensor or other suitable sensor separate from optical sensor(s) 211 on the underside of the device to estimate a contact condition between device 100 can the user's tissue. In some examples, one or more channels of optical sensor 211 can be used to estimate the contact condition. In some examples, measurements at wavelength λ3 (e.g., green light, blue light, etc.) can be used to estimate the contact condition (or more generally contribute to quality metrics) and identify which channels include measurements at wavelengths λ1 and λ2 (e.g., red light and IR light) that may be suitable for physiological signal processing and/or how to process the measurements at wavelengths λ1 and λ2 in the physiological signal processing. In some examples, when poor contact conditions are estimated based on wavelengths λ3 (e.g., when the device is outside a threshold distance from the surface of the user's skin or in poor contact) or based on another sensor (e.g., touch, proximity, force, etc.), the device can forgo estimating or reporting an estimated physiological characteristic based on wavelengths λ1 and λ2 (e.g., per channel or for all channels of the device). Although beats are shown, it is understood that the methods described herein can be applied based on instantaneous measurements, on a beat-by-beat basis, on an average of multiple beats, or after converting to a different domain, such as a frequency domain (e.g., using a Fourier transform) or wavelet domain.

Other conditions aside from contact condition may result in an inaccurate estimate of the physiological signal characteristic. For example, while device 100 is at an unexpected orientation relative to skin 120 or in the presence of transient or permanent tissue variations, measurements at wavelengths λ1 and λ2 (PPG signals) may result in inaccurate measurements of the physiological signal characteristic, despite the PPG signals having quality characteristics consistent with physiologically valid PPG signals showing a consistent cardiac signal indicative of accurate measurements of the physiological signal characteristic. In some examples, when this condition is detected, the device can forgo estimating or reporting an estimated physiological characteristic (e.g., under the assumption that the measurement may be inaccurate).

As described herein, in some examples, sensing of peripheral oxygen saturation may be performed using optical sensor in the background without user intervention (e.g., without a user request to estimate SpO2). The estimates of SpO2 can be used to monitor trends and/or provide notifications regarding SpO2 readings (e.g., if an SpO2 reading falls below a threshold). In some examples, the background sensing may be opportunistic, such that measurements by the optical sensor can occur based on detected conditions desirable for background sensing (e.g., separate from a user request to perform sensing of SpO2). For example, measurements of physiological signals by the optical sensor may be made when one or more criteria are satisfied that indicate conditions for a reliable SpO2 reading (e.g., when the device is on wrist, when the user is stationary, when the user in a favorable posture, and/or not interacting with the device including the optical sensor). In some examples, to reduce power consumption and/or to estimate a user's SpO2 readings throughout the day (or another period during which the wearable device 100 is worn), the measurements by the optical sensor can be spaced out in time. In some examples, a background measurement by the optical sensor can include collecting multiple windows of data (e.g., optionally using overlapping windows). The data from each window can be processed, and the results of processing can be combined to determine the SpO2 estimate. In some examples, a background measurement can be terminated earlier and/or processing of some of the measurements can be skipped to save power when sufficient physiological signals have been collected to generate an estimate of SpO2 or when the conditions during the measurement(s) indicate that the physiological signals are unlikely to yield a reliable estimate of SpO2.

Figure 4:
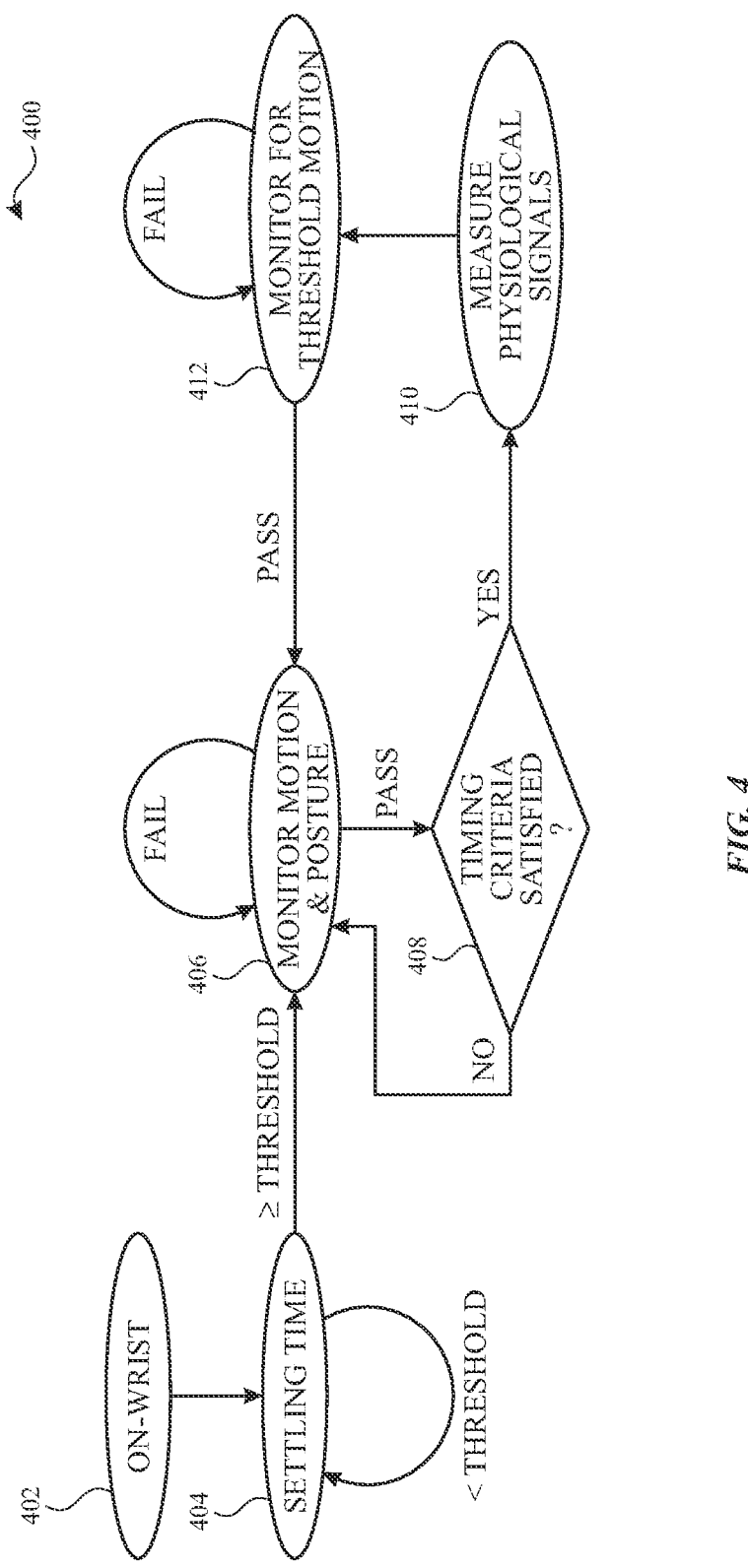
FIG. 4 illustrates an example state diagram for background sensing of peripheral oxygen saturation according to examples of the disclosure.

FIG. 4 illustrates an example state diagram 400 for background sensing of peripheral oxygen saturation according to examples of the disclosure. State diagram 400 includes states 402, 404, 406, 408, 410 and 412. In some examples, state diagram 400 can define one or more criteria to satisfy in order to initiate a first measurement of physiological sensors by an optical sensor or one or more subsequent measurements. In some examples, the one or more criteria can include an on-wrist criterion, a settling time criterion, motion and/or posture criteria, and one or more timing criteria. In some examples, satisfying the one or more criteria indicate conditions for successful, power-efficient background estimation of SpO2 (e.g., with a relatively high likelihood of generating a physiologically valid estimate of SpO2).

State 402 can represent a first state to detect whether a device (e.g., device 100 or 200) is fastened to user's wrist (e.g., using the optical sensor) or otherwise in contact/proximity with the user's wrist ("on-wrist") or not. Although primarily described in the context of whether the wearable device is on-wrist state, state 402 can more generally represent a state indicative of proximity/contact between the optical sensor and a user's tissue such that the optical sensor can be in a position to perform optical sensing of SpO2. When the device is detected on-wrist or otherwise in contact/proximity with the user's tissue (e.g., in the "on-wrist" state, satisfying the on-wrist criterion), the system can transition from state 402 to state 404. When the device is detected off-wrist or otherwise not in contact/proximity with the user's tissue (e.g., in the "off-wrist" state, failing to satisfy the on-wrist criterion), the system can remain in state 402. In some examples, when the off-wrist state is detected in a different state (e.g., states 404-412), the system can transition to state 402.

State 404 can represent a second state to detect whether a settling time criterion is satisfied after the device is on-wrist (or otherwise in position with respect to tissue to perform optical sensing). The system can remain in state 404 until the threshold period of settling time (e.g., 30 seconds, 5 minutes, 10 minutes, 30 minutes, etc.) has passed from the detection on the on-wrist state (e.g., while failing to satisfy the settling time criterion). The settling time can allow for improved signal quality (e.g., due to the tissue conforming to wearable device 100) and/or to allow the housing and/or electronics/ optics of device 100 to achieve thermal equilibrium with the tissue for improved performance. The system can transition from state 404 to state 406 upon the threshold period of settling time passing (e.g., satisfying the settling time criterion). State 404 can be used to delay the background optical sensing to save power.

State 406 can represent a third state to detect whether one or more motion and/or posture criteria are satisfied. For example, measurements by the optical sensor may be more likely to produce a valid and accurate SpO2 estimate while the user/device are stationary (e.g., motion less than a threshold). Additionally or alternatively, the measurements by the optical sensor may be more likely to produce a valid and accurate SpO2 estimate while in certain postures (or while not in certain postures). The system can remain in state 406 until the one or more motion and/or posture criteria are satisfied (e.g., while the one or more motion and/or posture criteria are not satisfied). The system can transition from state 406 to state 408 when the motion and/or posture criteria are satisfied.

State 408 can represent a fourth state to determine whether one or more timing criteria are satisfied to perform a new measurement using the optical sensor. For example, background measurements by the optical sensor may be spaced apart such that a threshold period of time must elapse after a successful estimate of SpO2 before attempting a new estimate of SpO2. In some examples, spacing out the measurements can reduce the correlation between SpO2 measurements (and potentially reduce the risk of an error in an earlier measurement reappearing in a subsequent measurement). Additionally or alternatively, spacing out the measurements can reduce the power consumption of background sensing (e.g., by capping the number of measurements in a given period of time, such as measurements per hour). The system can transition from state 408 back to state 406 when the one or more timing criteria are not satisfied. The system can transition from state 408 to state 410 upon satisfying the one or more timing criteria.

State 410 can represent a fifth state to perform the measurement of physiological signals using the optical sensor (e.g., after satisfying the on-wrist criterion, settling time criterion, motion and/or posture criteria, and one or more timing criteria). Performing the measurement of the physiological signals can include measuring, for each channel of the optical sensor(s) 211 (e.g., channels 108, 110, 112, and 114 for the configuration of FIG. 1B, channels 158, 160, 162 and 164 for the configuration of FIG. 1D, or channels 178A-178I for the configuration of FIG. 1E), light at two or more different wavelengths (e.g., red, IR, etc.). For example, the measurement can include a PPG signal for red and IR as illustrated in FIGS. 3A-3B, which can be used to compute physiological characteristics such as perfusion indices, perfusion index ratios, per-channel values ("cSpO2") estimating peripheral oxygen saturation using the physiological signals for each channel (e.g., using the perfusion index ratio for each channel), etc.

State 412 can represent a sixth state to detect whether an additional motion criterion is satisfied. For example, detecting motion above a threshold between measurements by the optical sensor may reduce the likelihood of repeating optical measurements in the same posture with the same orientation between the device and the tissue. Changing the posture and/or the orientation between the device and the tissue can reduce the likelihood of erroneous successive optical measurements (e.g., due to a transient tissue anomaly). The system can remain in state 412 when the additional motion criterion is not satisfied (e.g., while motion is less than a threshold motion, or optionally while motion is greater than the threshold motion for less than a threshold period of time). The system can transition from state 412 to state 406 when the motion and/or posture criteria are satisfied (e.g., when motion is greater than the threshold motion, optionally for more than a threshold period of time). In some examples, the system can also transition from state 412 to state 406 after a timeout even when the additional motion threshold is not satisfied.

It is understood that state diagram 400 can be performed at an electronic device such as device 100 or 200 (e.g., by processor 210 and/or by signal processor 214, or in any other circuitry configured to implement a state machine). It should be understood that the particular order of the description of the operations in the state diagram is merely exemplary and is not intended to indicate that the described order is the only order in which the operations could be performed. One of ordinary skill in the art would recognize various ways to reorder the operations described herein (e.g., some operations of state diagram 400 can be combined, reordered and/or omitted). In some examples, state 404 can be omitted (e.g., equivalent to setting the settling time to zero) or state 412 can be omitted. In some examples, states 406 and 408 can be combined or reordered.

Referring back to state 406, the one or more motion and/or posture criteria can be based on motion and/or orientation data from one or more motion or orientation sensors (e.g., motion and/or orientation sensors 230). In some examples, the one or more motion and/or posture criteria can include a first motion criterion that is satisfied when the motion of the user/device 100 is less than a threshold motion, optionally for a threshold period of time.

In some examples, the measure of motion can be a maximum variance from a multi-channel accelerometer. The maximum variance can be computed for each motion monitoring window. For example, the motion data can be divided into N motion monitoring windows (optionally non-overlapping) that include M samples of acceleration in each dimension (X, Y, Z) of a three-channel accelerometer. In some examples, the motion monitoring window can be between 1-30 seconds in duration. In some examples, the motion monitoring window can be between 1-10 seconds in duration. In some examples, the motion monitoring window can be between 2-5 seconds in duration.

The maximum variance of the M sample values for each channel of the motion monitoring window can be computed using equation (1):

$$\sigma^2_{max} = \max\left(\sigma^2_X, \sigma^2_Y, \sigma^2_Z\right) = \tag{1}$$

$$\max\left(\frac{\sum_{i=1}^{M}\left(X_i - \bar{X}\right)^2}{M}, \frac{\sum_{i=1}^{M}\left(Y_i - \bar{Y}\right)^2}{M}, \frac{\sum_{i=1}^{M}\left(Z_i - \bar{Z}\right)^2}{M}\right)$$

where $\sigma_{max}^2$ represents the maximum variance for the multiple channels of the motion monitoring window, $\sigma_X^2$, $\sigma_Y^2$, $\sigma_Z^2$ represent the variance for x-axis, y-axis, and z-axis accelerometer channels, respectively, M represents the number of samples in the motion monitoring window, $X_i$, $Y_i$ and $Z_i$ represent the accelerometer measurements for a sample for x-axis, y-axis, and z-axis accelerometer channels, respectively, and, and $\bar{X}$, $\bar{Y}$, $\bar{Z}$ represent the mean for x-axis, y-axis, and z-axis accelerometer channels for the motion monitoring window. In some examples, the accelerometer signals can be filtered (e.g., using a low-pass filter, high-pass filter, and/or band-pass filter) before computing the measure of motion (e.g., variances for the three-channel accelerometer).

In some examples, the first motion criterion can be satisfied when the maximum variance is less than a threshold variance. The threshold variance can be determined empirically. In some examples, the threshold variance can be between 0.0001 and 0.01. In some examples, the threshold variance can be between 0.0005 and 0.005. In some examples, the first motion criteria can be satisfied when the maximum variance is less than the threshold variance for a threshold period of time (e.g., a threshold number of consecutive motion monitoring windows). In some examples, the threshold period of time is between ten seconds and two minutes. In some examples, the threshold period of time is between 15 seconds and 60 seconds. In some examples, the threshold period of time is between 20 and 40 seconds.

In some examples, the one or more motion and/or posture criteria can include a posture criterion. In some examples, the posture criterion can be satisfied when certain postures are detected or while certain postures are excluded. For example, measurements of SpO2 may be negatively impacted while a user wrist is rotated such that gravity pulls the optical sensor away from the surface of the wrist. This posture may be referred to herein as "upside-down wrist." Additionally, or alternatively, measurements of SpO2 may be negatively impacted while a user's arm hangs downward or is raised upward. These postures may be referred to herein as "hanging arm" and "raised arm," respectively. It is understood that the "upside-down wrist," "hanging arm" and "raised arm" have some tolerance defining the amount of rotation of the wrist or the angle of the arm (e.g., with respect to gravity). Thus, it may be desirable to avoid measuring SpO2 in these postures. In some examples, the postures can be estimated based on one or more motion or orientation sensors (e.g., motion and/or orientation sensors 230, IMU, etc.). For example, assuming that the device is oriented such that the Z axis accelerometer is oriented downward from the backside of device 100, the upside-down wrist posture can be detected when the measurement of acceleration Z>0. For example, assuming the device is oriented such that the X-axis accelerometer is oriented along the user's arm, the raised arm or handing arm postures can be detected when the absolute value of the average X-axis accelerometer for the motion monitoring window (|X̄|) is greater than a threshold (e.g., $$\frac{1}{\sqrt{2}}$$

to detect the arm within approximately 45 degrees of the arm hanging straight down or raised straight up). Thus, for the above examples, the disfavored upside-down wrist, hanging arm and raised arm postures can be excluded when acceleration Z<0 and the magnitude of X-axis accelerometer for the motion monitoring window is less than the threshold. In some examples, the disfavored postures may need to be excluded (e.g., using the accelerometer channels and thresholds described above) for a threshold period of time to satisfy the posture criterion (e.g., a threshold number of consecutive motion monitoring windows). In some examples, the threshold period of time is between ten seconds and two minutes. In some examples, the threshold period of time is between 15 seconds and 60 seconds. In some examples, the threshold period of time is between 20 and 40 seconds. It is understood that the favored or disfavored postures may be different for optical sensors disposed on tissue other than the wrist. Additionally, it is understood that the thresholds could be different than the example thresholds above. For example, the threshold can be adjusted to allow more or less tolerance from the arm hanging straight up or straight down (e.g., may permit 30° tolerance) or may require a threshold negative Z value (rather than simply any negative Z value).

Referring back to state 412, the additional motion criterion can be based on motion data from the one or more motion or orientation sensors (e.g., motion and/or orientation sensors 230). In some examples, the additional motion criterion can be satisfied when the motion of the user/device 100 is greater than a threshold motion, optionally for a threshold period of time (e.g., a threshold number of consecutive motion monitoring windows). In some examples, the measure of motion can be a maximum variance from a multi-channel accelerometer as described above with respect to equation (1). In some examples, the additional motion criterion can be satisfied when the maximum variance is greater than a threshold variance (the same or a different threshold variance as used for the motion criterion at state 406). The threshold variance can be determined empirically. In some examples, the threshold variance can be between 0.01 and 0.5. In some examples, the threshold variance can be between 0.05 and 0.1. In some examples, the additional motion criterion can be satisfied when the maximum variance is greater than the threshold variance for a threshold period of time. In some examples, the threshold period of time is between one second and one minute. In some examples, the threshold period of time is between 5 seconds and 15 seconds.

Referring back to state 408, in some examples, the one or more timing criteria can include a first timing criterion that can be satisfied when the last successful measurement of the optical sensor occurs more than a first threshold period of time ago (e.g., at least the first threshold period of time passes from the prior successful measurement of the optical sensor). In some examples, a successful measurement of the optical sensor can correspond to measurement of physiological signals (e.g., corresponding to state 410) for the full duration (e.g., without early termination due to motion and/or unfavorable posture) to generate physiological signals of threshold quality such that a background SpO2 can be estimated for the measurement. In some examples, the first threshold period of time can be between 10 minutes and 120 minutes. In some examples, the first threshold period of time can be between 15 minutes and 90 minutes. In some examples, the first threshold period of time can be between 20 minutes and 60 minutes. As described herein, spacing out the measurements reduce the correlation between SpO2 measurements (and potentially reduce the risk of an error in an earlier measurement reappearing in a subsequent measurement). Additionally or alternatively, spacing out the measurements can reduce the power consumption of background sensing.

In some examples, the one or more timing criteria can include a second timing criterion that can be satisfied when the number of measurements by the optical sensor (e.g., number of visits to state 410) within a threshold period of time is less than a threshold number. For example, the threshold number can be in units of optical sensor measurement cycles per hour. In some examples, the threshold number can be between 2-10 measurements per hour. In some examples, the threshold number can be between 2-4 measurements per hour. Reducing the number of permitted optical sensor measurement cycles per hour can reduce power consumption.

Referring back to state 410, the measurement of physiological signals can, in some examples, include measuring physiological signals (e.g., a PPG signal at a red wavelength and a PPG signal at an IR wavelength) for multiple channels (e.g., the four channels of the configuration of FIGS. 1B, 1D, the nine channels of the configuration of FIG. 1E, or a different number of channels for a different configuration) for a first duration. In some examples, the SpO2 can be estimated using the physiological signals from the multiple channels for the first duration. In some examples, each background measurement of physiological signals can include acquiring multiple, optionally overlapping, windows of optical data, with each of the windows of the first duration. In some examples, measuring multiple windows can include measuring the physiological signals for a second, longer duration than the first duration. Each of the multiple windows of the first duration (or equivalent first duration portions of the second, longer duration) can be used to estimate a per-window value ("wSpO2" values) estimating peripheral oxygen saturation for each window. For example, each wSpO2 values can be computed using the cSpO2 values for the channels measured during each window. In some examples, the each of the windows of optical data of the first duration can be used to estimate a wSpO2 value, and the multiple wSpO2 values can be combined (e.g., averaged) to estimate an SpO2 value for the background sensing operation of the second duration.

In some examples, the measurement of the physiological sensors (at state 410) can be terminated early to save power. For example, the measurements can be terminated when user movement is detected during the measurements. Additionally or alternatively, the measurements can be terminated when sufficient enough data (or enough reliable data) has been collected to estimate accurately estimate SpO2 already (e.g., a threshold number of windows of optical data).

Figure 5:
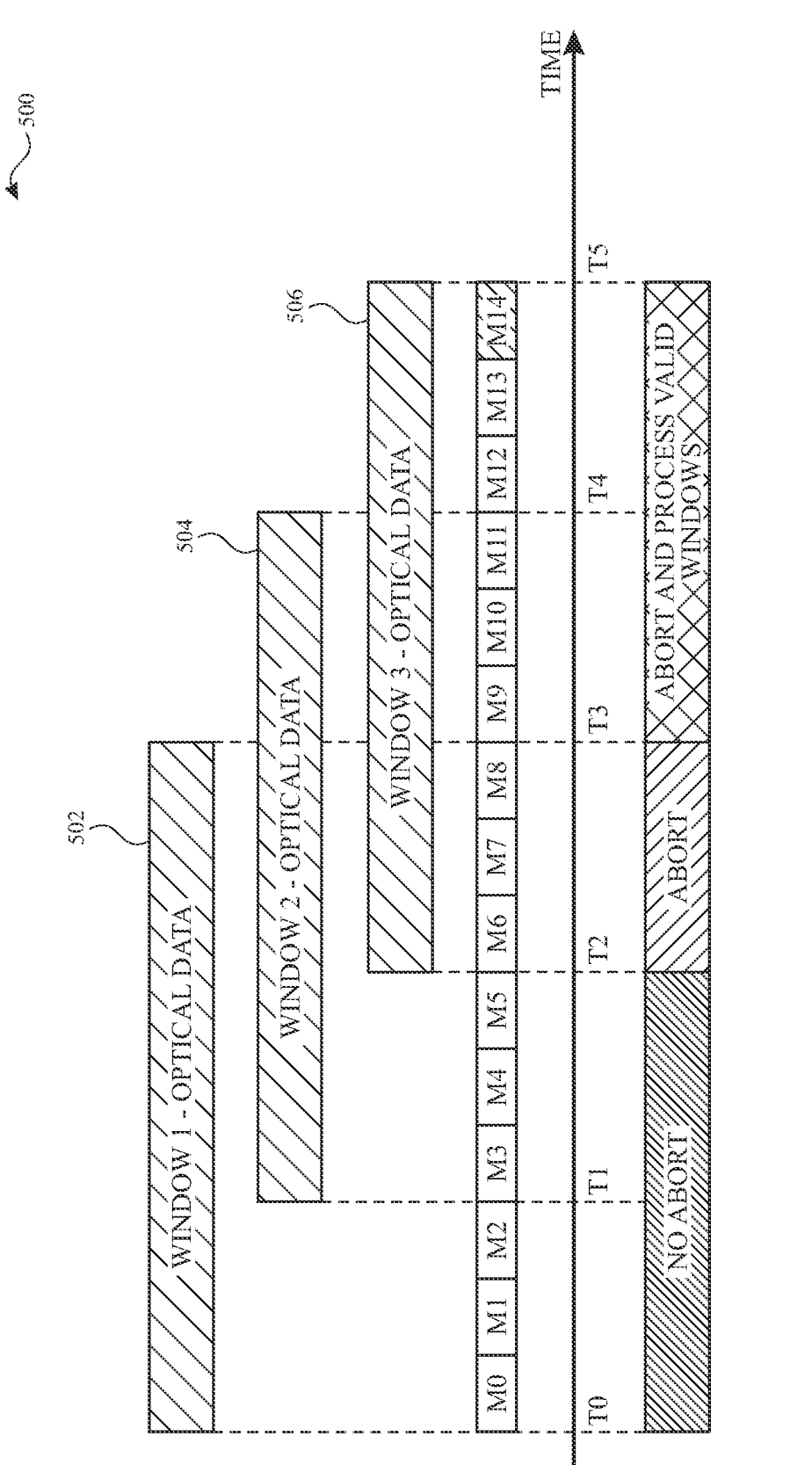
FIG. 5 illustrates an example timing diagram for measurement of physiological signals according to examples of the disclosure.

FIG. 5 illustrates an example timing diagram 500 for measurement of physiological signals according to examples of the disclosure. Timing diagram 500 illustrates three overlapping windows of physiological signals (optical data) from the optical sensor. Each window can be of the first duration and the multiple windows together (e.g., from the start of the first window to the end of the last window in a measurement cycle) can be of the second duration. For example, a first window 502 can correspond to optical data acquired between TO and T3, a second window 504 can correspond to optical data acquired between T2 and T4, and a third window 506 can correspond to optical data acquired between T3 and T5, such that the three overlapping windows can correspond to optical data acquired between TO and T5. Each window can include physiological signal measurements for a plurality of optical channels (e.g., red and IR PPG signals for the multiple channels) and the physiological signal measurements of each window can be processed as described herein to produce a wSpO2 value. The multiple wSpO2 values can be combined (e.g., averaged) to estimate a background SpO2.

As described herein, in some examples, motion can be monitored during measurement of the physiological signals. In some examples, motion during a window can indicate that the corresponding physiological signals of the window are unsuitable for estimating a wSpO2 value. For example, timing diagram 500 illustrates motion monitoring windows M0-M14. In some examples, during each of the motion monitoring windows, motion data (e.g., accelerometer data)

can be acquired. In some examples, a measure of motion, such as a maximum variance described herein with respect to equation (1), can be computed for each motion monitoring windows. In some examples, when the measure of motion data exceeds a threshold (e.g., the same threshold as the first motion criterion described with respect to state 406), the data in the corresponding window(s) of physiological signals/optical data that overlap in time can be flagged as unreliable data (e.g., unsuitable for estimating SpO2 due to potentially motion related corruption). For example, detecting more than a threshold motion in any of motion monitoring windows M1-M8 can cause the optical data of window 502 to be flagged as unreliable, detecting more than a threshold motion in any of motion monitoring windows M3-M11 can cause the optical data of window 504 to be flagged as unreliable, and detecting more than a threshold motion in any of windows M6-M14 can cause the optical data of window 506 to be flagged as unreliable. Due to the overlapping windows of FIG. 5, three windows 502-506 can be flagged as unreliable when detecting more than a threshold motion in any of motion monitoring windows M6-M8, and two windows 502-504 or 504-506 can be flagged as unreliable when detecting more than a threshold motion in any of motion monitoring windows M3-M5 or M9-M11, respectively.

In some examples, motion during a window can cause the acquisition of physiological signals to be terminated in whole or in part. In some examples, when the measure of motion data exceeds a threshold, the acquisition of physiological signals can be terminated for the remainder of the measurement cycle. For example, detecting motion at motion monitoring window M1 can cause termination of measuring physiological signals by the optical sensor for window 502 (interrupting the measurement of physiological signals) and forgoing measurement of physiological signals for windows 504-506. In a similar manner, detecting motion at motion monitoring window M9 can cause termination of measuring physiological signals by the optical sensor for window 504-506 (interrupting the measurement of physiological signals).

In some examples, when the measure of motion data exceeds a threshold, the acquisition of physiological signals can be terminated for the corresponding window(s). For example, detecting motion at motion monitoring window M1 can cause termination of measuring physiological signals by the optical sensor for window 502 (interrupting the measurement of physiological signals), but subsequently proceeding to measure (or at least attempt to measure) physiological signals for windows 504-506. Detecting motion at motion monitoring window M9 can cause termination of measuring physiological signals by the optical sensor for window 504-506 (interrupting the measurement of physiological signals).

In some examples, when terminating the acquisition of physiological signals in whole or in part due to detecting motion, the detection and/or processing of motion data may be terminated or paused. For example, subsequent measurement of motion can be terminated or paused while the acquisition of physiological signals is terminated or paused.

In some examples, whether to terminate the remainder of the measurement of physiological signals or to resume measurement of physiological signals for a later window that is not coincident with motion above a threshold, may be dependent on whether one or more complete windows of optical data were successfully acquired prior to the detection of motion and/or whether one or more subsequent windows of data can be successfully collected after the detection of motion. For example, detecting motion above the threshold at T4 may result in unreliable data for windows 502 and 504, but the measurement can continue, in some examples, to attempt to measure data for the third window 506 (because window 506 have not yet been deemed unreliable due to motion and/or because both windows 502-504 have been indicated to be unreliable). In some examples, detection motion above the threshold detected at T10 may result in termination of the measurement because window 502 appears to have reliable data (without motion above a threshold) and/or because the remaining windows have been indicated to be unreliable.

In some examples, the SpO2 estimation based on windows 502-506 may be dependent on whether sufficient reliable data (e.g., without motion above a threshold) has been collected. In some examples, the system may forgo SpO2 estimation when no data or insufficient data has been collected.

In some examples, as different states indicated below the timeline of timing diagram 500, can represent the system behavior in response to motion above a threshold during the measurement of physiological signals. For example, measuring of physiological signals can continue without aborting or terminating the measurement of physiological signals (e.g., at 410) when detecting motion above the threshold in any of motion monitoring windows M0-M6 (e.g., no abort/termination state from T0-T2). Although the first window 502 and/or second window 504 may include unreliable data due to motion, the subsequent measurements may allow for the second window 504 and/or third window 506 to acquire reliable data (e.g., without a threshold motion). The reliable window(s), if any, can be subsequently processed for SpO2 measurements. Measuring of physiological signals can be aborted or terminated when detecting motion above the threshold in any of motion monitoring windows M6-M8 (e.g., abort/termination state from T2-T3). Detecting motion above the threshold in this time period can render each of windows 502-506 unreliable (and thus the continued measurement and subsequent processing for SpO2 may be futile). Measuring of physiological signals can be aborted or terminated when detecting motion above the threshold in any of motion monitoring windows M9-M14 (e.g., also an abort/termination state from T3-T5). Detecting motion above the threshold in this time period renders the remaining windows 504-506 unreliable. However, earlier reliable windows of physiological signals (e.g., window 502) may be subsequently processed for SpO2.

It should be understood that timing diagram 500 is an example and other variations are possible. For example, although three overlapping windows are shown, in some examples, more or fewer windows can be used (e.g., one, two, four, five, etc.) and the windows may overlap more, less, or not at all. Additionally, although the timing diagram illustrates nine motion monitoring windows for each of windows 502, 504 and 506, it should be understood that the relative durations of the motion monitoring windows to each of windows 502, 504 and 506 can be different (e.g., could be a 1:1: ratio, 2:1 ratio, 3:1 ratio, etc. instead of the 9:1 ratio illustrated in FIG. 5). Additionally, it should be understood that the final motion monitoring window (M14) may be used to flag the final window of optical data as unreliable data unsuitable for estimating SpO2, but it may not be used to terminate the measurement of physiological signal because the measurement concludes in at approximately the same time as the conclusion of final motion monitoring window (M14). It is also understood that the designation of different states representing system behavior in response to motion above a threshold can also be different based on the above variations (e.g., in number of windows, relative timing of windows, etc.) and/or depending on how sensitive the system is to motion. For example, in some examples, detecting motion during any of the motion monitoring windows can cause the measurement to terminate early even when the possibility exists for acquisition of optical data in a later window that does not overlap in time with the detected threshold motion.

Although the above discussion focuses primarily on motion above a threshold to indicate that the corresponding physiological signals of the window are unsuitable for estimating SpO2, in some examples, detecting a change to an unfavorable posture during a window can also indicate that the corresponding physiological signals of the window are unsuitable for estimating SpO2 (e.g., the discussion of monitoring motion can be extended to cover the motion and/or posture criteria during the measurement of the physiological signals).

Additionally or alternatively, the measurement of physiological signals can terminate early when the signal quality measured at the channels during a window is poor (e.g., less than a threshold). In some examples, one or more quality metrics can be calculated for the multiple channels. In some examples, the quality metric can be a quality score (e.g., between zero and one) with higher scores corresponding to physiologically valid PPG signals showing a consistent cardiac signal. In some examples, the channel quality score can be determined based on one or more quality metrics including: the signal-to-noise ratio (SNR) of the optical sensor hardware, the morphology of the PPG signals, the phase consistency between the PPG signals at different wavelengths (e.g., red, IR, green), correlation between the PPG signals at different wavelengths (e.g., red, IR, green), beat-to-beat consistency (correlation of heartbeats) in the PPG signal, and/or harmonic consistency in the PPG signal. In some examples, a window with channel(s) with quality metrics/quality scores below a threshold(s) can be discarded and not used for estimating an SpO2 value and/or can cause the early termination of the measurement of the physiological signals (e.g., under the assumption that the poor signal quality of the earlier measurements continue into the later measurements).

In some examples, the duration of the windows 502-506 and/or the number of windows 502-506 in a background measurement of physiological signals can be dynamically adjusted based on signal quality. For example, longer duration windows and/or more windows can be used when signal quality is poorer and short duration windows and/or fewer windows can be used when signal quality is more robust.

Figure 6A:
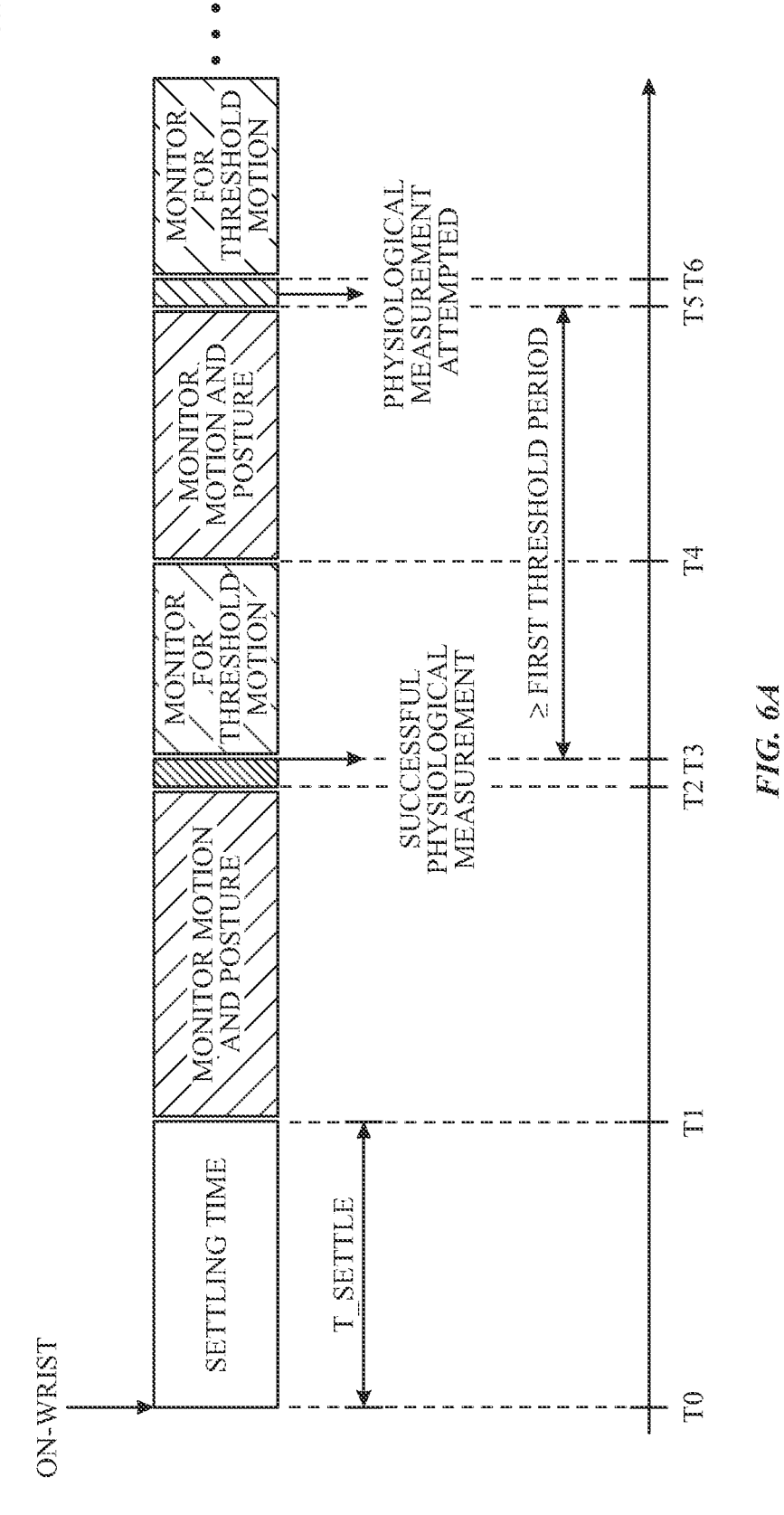
FIGS. 6A-6C illustrate timing diagrams of example operation of a state diagram of FIG. 4 according to examples of the disclosure.
Figure 6B:
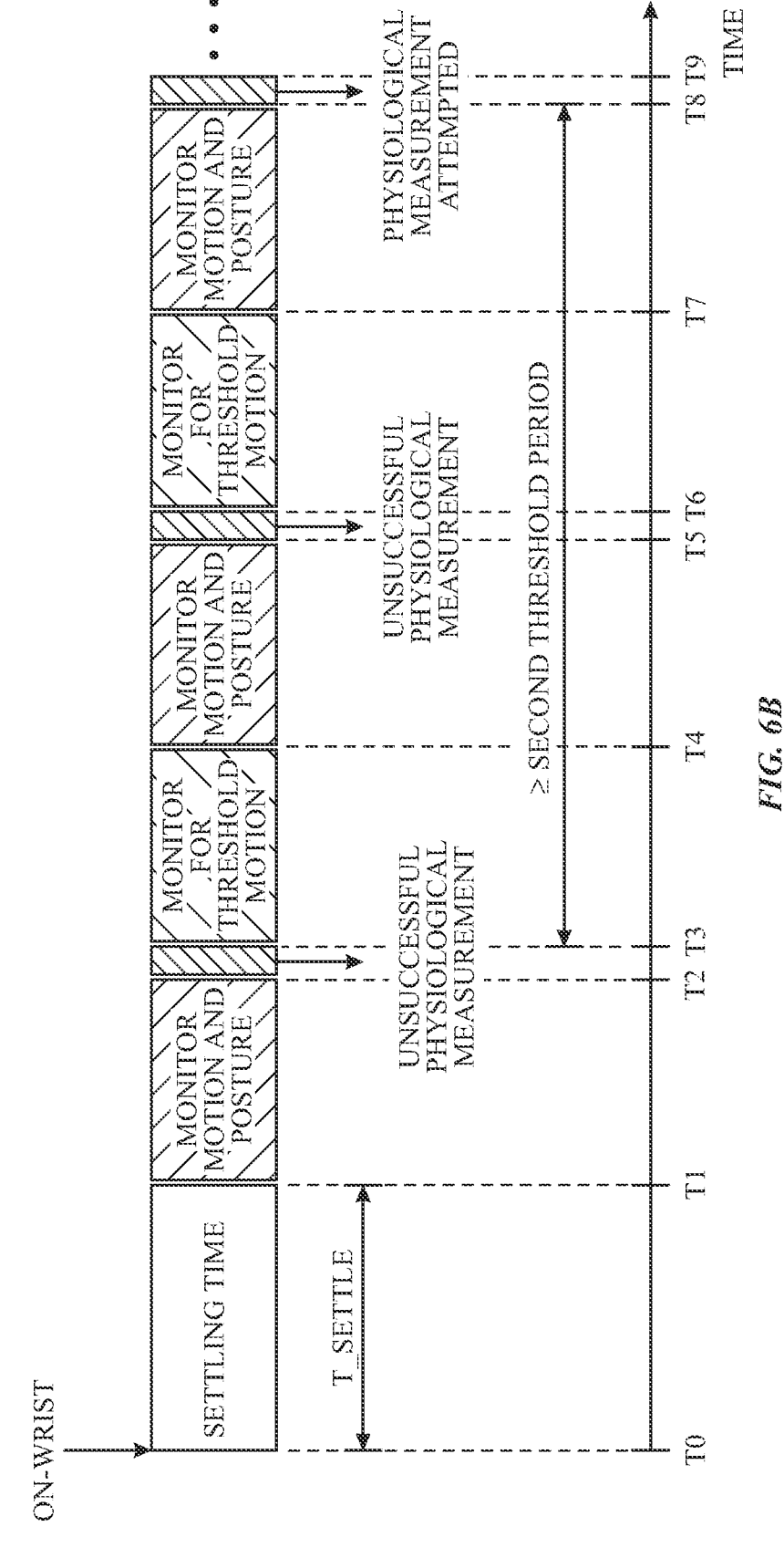
Figure 6C:
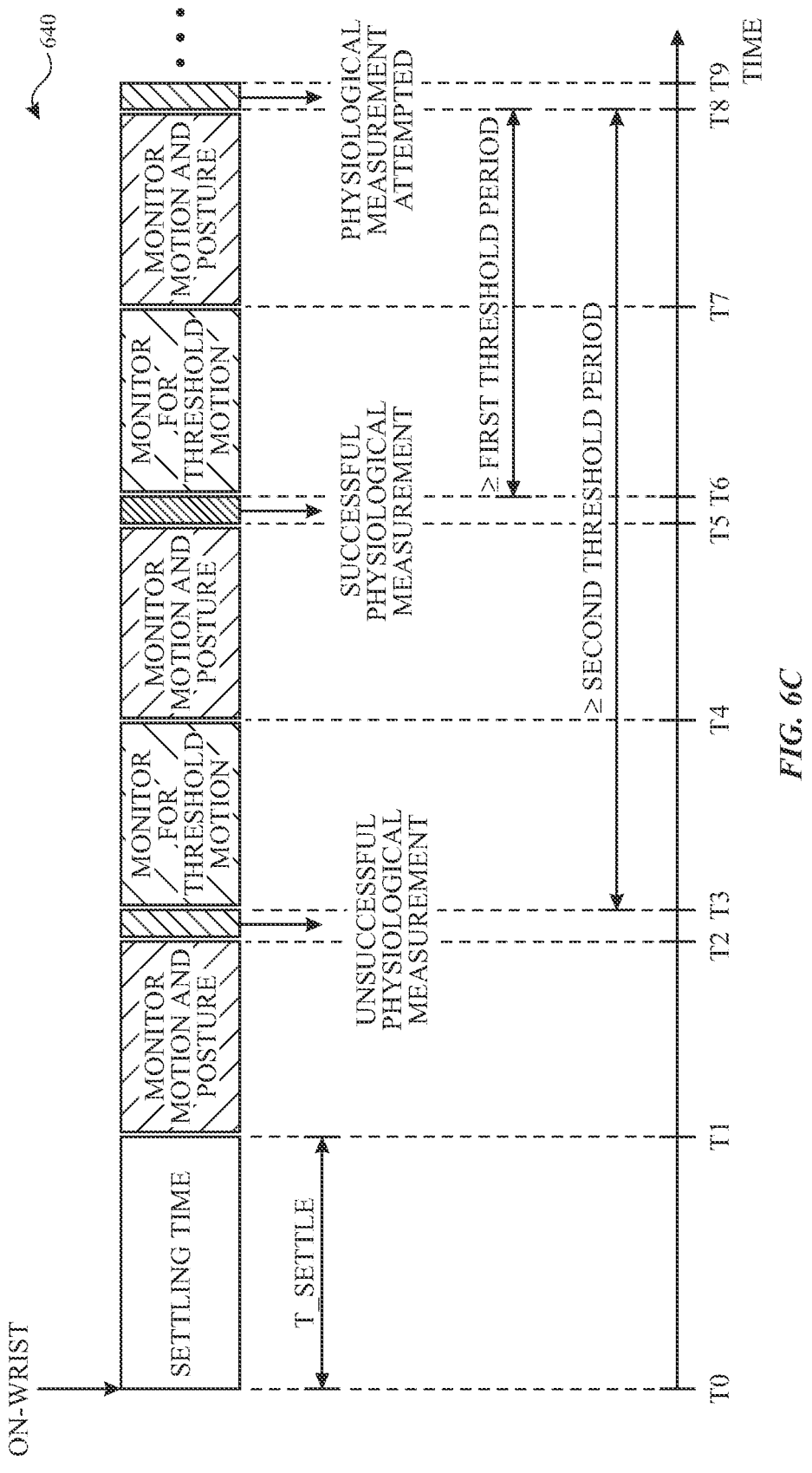

FIGS. 6A-6C illustrate timing diagrams 600, 620, and 640 of example operation of state diagram 400 according to examples of the disclosure. Timing diagram 600 corresponds to a first successful measurement, timing diagram 620 corresponds to multiple unsuccessful measurements, and timing diagram 640 corresponds to a first unsuccessful measurement followed by a first successful measurement. A successful measurement can correspond to measurement of physiological signals (e.g., corresponding to state 410) for the full duration (e.g., without early termination due to motion and/or unfavorable posture) to generate physiological signals of threshold quality such that a background SpO2 can be estimated for the measurement. In contrast, an unsuccessful measurement of physiological signals can correspond to measurement of physiological signals for less than the full duration (e.g., with early termination due to motion and/or unfavorable posture) or generating physiological signals with less than the threshold quality such that a background SpO2 cannot be estimated.

In timing diagram 600 of FIG. 6A, at TO, the system can detect a device (e.g., device 100, 200) "on-wrist" corresponding to the transition from state 402 to state 404. From T0 to T1, the system can wait for the settling time T_SETTLE to pass corresponding to remaining in state 404. At T1, the system can transition to monitoring motion and/or posture corresponding to transitioning from state 404 to state 406. The system can monitor motion and/or posture until the motion and/or posture criteria is satisfied at T2. The system can then determine whether the timing criteria are satisfied. For a first attempt following on-wrist without any prior measurement attempts for background SpO2, the system can satisfy the timing criteria and the system can transition to perform a measuring of physiological signals corresponding to state 410. In the example of FIG. 6A, the system can perform a successful measurement of physiological signals between T2 and T3.

The system can attempt a subsequent measurement of physiological signals to estimate background SpO2 from T5-T6 (e.g., corresponding to returning back to state 410). At T3, the system can monitor for more than a threshold motion corresponding to state 412. At T4, after detecting more than the threshold motion (e.g., satisfying the additional motion criterion), the system can transition to state 406. At T4, the system can monitor motion and/or posture until the motion and/or posture criteria are satisfied at T5. The system can then determine whether the timing criteria are satisfied. For a second attempt following a first successful background SpO2 measurement, the system can satisfy the timing criteria, for example, when the elapsed time from the first successful background measurement is greater than a threshold (e.g., T5–T3≥a first threshold period), and when the number of attempted measurements is less than a threshold number per hour (e.g., two times per hour, three times per hour, etc.). When the timing criteria are satisfied, the system can transition to attempt measuring of physiological signals (e.g., between T5 and T6).

In timing diagram 620 of FIG. 6B, the system can operate in the same manner as FIG. 6A from T0-T2 (e.g., detecting the device on-wrist, detecting passage of the settling time, satisfaction of motion and/or posture criteria, and satisfaction of the timing criteria). In FIG. 6B, the system can perform a first unsuccessful measurement of physiological signals between T2 and T3 (e.g., motion and/or posture criteria are not satisfied during the measurement of the optical sensor, etc.).

The system can attempt a subsequent measurement of physiological signals to estimate background SpO2 from T5-T6 (e.g., after detecting satisfaction of the additional motion criterion and satisfaction of the motion and/or posture criteria in a similar manner as in FIG. 6A). At T5, the system can determine whether the timing criteria are satisfied. For a second attempt following a first unsuccessful background SpO2 measurement, the system can satisfy the timing criteria, for example, when the number of attempted measurements is less than a threshold number per hour. When the timing criteria are satisfied, the system can transition to attempt measuring of physiological signals (e.g., between T5 and T6). In FIG. 6B, the system performs a second unsuccessful measurement of physiological signals (e.g., motion and/or posture criteria are not during the measurement of the optical sensor, etc.).

The system can attempt a subsequent measurement of physiological signals to estimate background SpO2 from T8-T9 (e.g., after detecting satisfaction of the additional motion criterion and satisfaction of the motion and/or posture criteria). At T8, the system can determine whether the timing criteria are satisfied. For a third attempt following first and second unsuccessful background SpO2 measurements, the system can satisfy the timing criteria, for example, when the number of attempted measurements is less than a threshold number per hour (e.g., when T8–T3>a second threshold period, for an example with a threshold of two measurements per second threshold period). When the timing criteria are satisfied, the system can attempt measuring of physiological signals (e.g., between T8 and T9).

In timing diagram 640 of FIG. 6C, the system can operate in the same manner as FIG. 6B from T0-T5 (e.g., detecting the device on-wrist at T0, detecting passage of the settling time at T1, satisfaction of motion and/or posture criteria and of the timing criteria at T2, performance of a first unsuccessful measurement between T2 and T3, satisfaction of the additional motion criterion at T4, and satisfaction of the motion and/or posture criteria and the timing criteria at T5). In FIG. 6C, unlike in FIG. 6B, the system can perform a first successful measurement of physiological signals between T5 and T6.

The system can attempt a subsequent measurement of physiological signals to estimate background SpO2 from T8-T9 (e.g., after detecting satisfaction of the additional motion criterion and satisfaction of the motion and/or posture criteria in a similar manner as in FIGS. 6A-6B). At T8, the system can determine whether the timing criteria are satisfied. For a third attempt following first unsuccessful measure of background SpO2 and a first successful measure, the system can satisfy the timing criteria, for example, when the elapsed time from the first successful background measurement is greater than a threshold (e.g., T8–T6≥a first threshold period), and when the number of attempted measurements is less than a threshold number per hour (e.g., when T8–T3>a second threshold period, for an example with a threshold of two measurements per second threshold period). When the timing criteria are satisfied, the system can attempt measuring of physiological signals (e.g., between T8 and T9).

Figure 7:
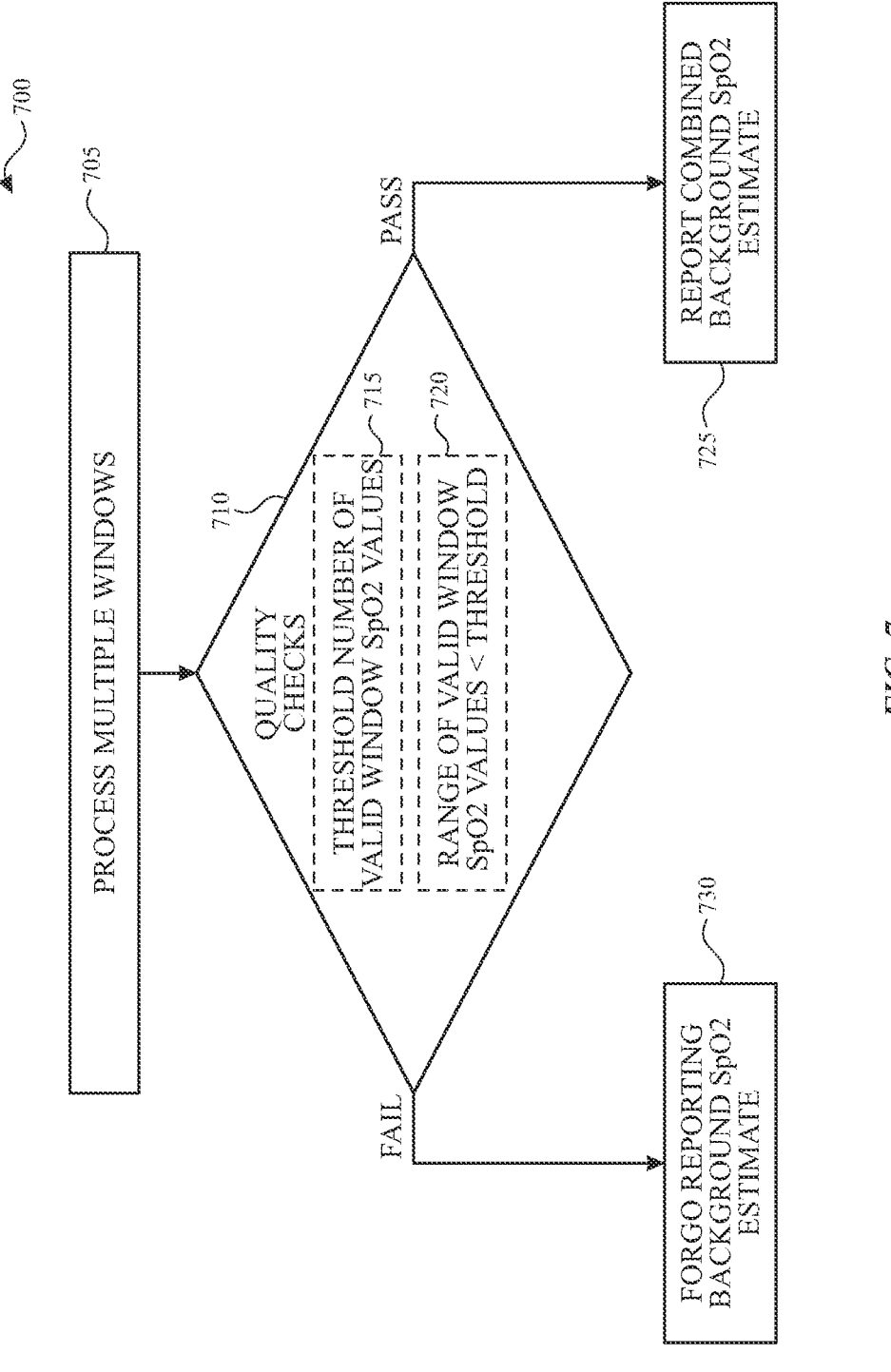
FIG. 7 illustrates an example process for estimating background peripheral oxygen saturation for multiple windows according to examples of the disclosure.

Referring back to FIG. 5, in some examples, the data from multiple windows (e.g., windows 502, 504 and 506) can be processed to estimate background SpO2. FIG. 7 illustrates an example process 700 for estimating SpO2 for multiple windows according to examples of the disclosure. In some examples, after measuring the physiological signals (e.g., corresponding to state 410 and according the timing diagram 500), the system can process the physiological signals (optical data) for the multiple windows at 705. For example, each window can include data from multiple channels (e.g., from all channels of the optical sensor), with the data including PPG signals for red and IR wavelengths. In some examples, the processing for a window can include estimating per-channel values ("cSpO2" values) for each channel in the window (e.g., using a red-to-IR PI modulation ratio for each channel in the window), and a wSpO2 value can be computed for the window from a combination of the cSpO2 values for the channels in the window (e.g., an average of the cSpO2 values). The same processing can be completed for each window.

In some examples, as described herein with respect to FIG. 5, measurement of the physiological signals may be terminated early. For some such windows the processing may be skipped (e.g., an estimated wSpO2 for the window is not available) because the data for the window was never acquired or because the acquired data for the window is flagged as including unreliable data (e.g., unsuitable for estimating SpO2 due to potentially motion and/or posture related corruption).

In some examples, the processing may be performed but the processing may fail to produce a physiologically valid wSpO2 value (e.g., due to poor signal quality of the physiological signals, etc.). In some examples, one or more quality metrics can be calculated for the multiple channels. In some examples, the quality metric can be a quality score (e.g., between zero and one) with higher scores corresponding to physiologically valid PPG signals showing a consistent cardiac signal. In some examples, the channel quality score can be determined based on one or more quality metrics including: the signal-to-noise ratio (SNR) of the optical sensor hardware, the morphology of the PPG signals, the phase consistency between the PPG signals at different wavelengths (e.g., red, IR, green), correlation between the PPG signals at different wavelengths (e.g., red, IR, green), beat-to-beat consistency (correlation of heartbeats) in the PPG signal, and/or harmonic consistency in the PPG signal. In some examples, channels with quality metrics/quality scores below a threshold(s) can be discarded and not used for estimating a cSpO2 value. As a result, the processing of a window may fail to produce a wSpO2 value for the window due to poor signal quality (e.g., a signal quality score less than a threshold).

In some examples, at 710, quality checks can be performed on the results of processing the multiple windows. In some examples, the quality checks can include, at 715, a determination of whether a threshold number of physiologically valid wSpO2 estimates result from the processing of multiple windows. In some examples, the threshold can be one physiologically valid wSpO2 estimate for one window. In some examples, the threshold can be multiple physiologically valid wSpO2 estimates for multiple windows (e.g., two, three, etc.). A window that is not processed or cannot be processed to generate a physiologically valid SpO2 (e.g., due to signal quality issues and/or motion/posture corruption during measurement) can be excluded from the count of physiologically valid wSpO2 estimates. In some examples, the quality checks can include, at 720, a determination of whether a range of physiologically valid wSpO2 values is less than a range threshold. The range of the wSpO2 values can be computed as the difference between the maximum wSpO2 value and the minimum wSpO2 value among the physiologically valid wSpO2 values (assuming there are multiple physiologically valid wSpO2 values). In some examples, the threshold can be set between 0%-15% SpO2. In some examples, the threshold can be set between 2%-10% SpO2.

In accordance with a determination that the processing results in at least the threshold number of physiologically valid wSpO2 estimates and that the range of physiologically valid wSpO2 values is less than the range threshold, the system can compute a combined SpO2 estimate (e.g., averaging the physiologically valid wSpO2 estimates) and can report the background SpO2 estimate at 725. In some examples, the estimated background SpO2 can be reported to the user at 535 (e.g., displayed on the display, can be stored on the device or transmitted to another device, or can be reported with other feedback mechanisms (e.g., audio feedback, haptic feedback, etc.)). In accordance with a determination that the processing results in less than a threshold number of physiologically valid wSpO2 estimates or that the range of physiologically valid wSpO2 values is greater than the range threshold, the system can forgo computing a combined SpO2 estimate and/or forgo reporting the background SpO2 estimate at 730.

It is understood that process 700 can be performed at an electronic device such as device 100 or 200 (e.g., by processor 210 and/or by signal processor 214). It should be understood that the particular order of the description of the operations in the state diagram is merely exemplary and is not intended to indicate that the described order is the only order in which the operations could be performed. One of ordinary skill in the art would recognize various ways to reorder the operations described herein (e.g., some operations of process 700 can be combined, reordered and/or omitted). In some examples, different or no quality checks can be performed at 710. In some examples, a background SpO2 estimate can be made from a combination of the multiple wSpO2 values for the windows, and the quality check(s) can be performed on the background SpO2 estimate (e.g., to determine that the SpO2 estimate is physiologically valid).

Referring back to the state diagram of FIG. 4 and the timing diagram of FIG. 5, it should be understood that that additional criteria can be used as a prerequisite for beginning measurement of the physiological signals (at state 410) and/or for early termination. The additional criteria can also improve performance of the background SpO2 measurement and save power by performing the measurements when most likely to succeed (and not performing the measurements otherwise). For example, optical signal quality can be measured before and/or during the measurement of the physiological signals at state 410, such that the measurement of physiological signals begins and/or continues only when the signal quality is above a threshold. For example, the signal quality can provide an indication of band tightness (e.g., how well the optical sensor is fastened to the tissue) and/or ambient light conditions which may interfere with the measurement of physiological signals. In some examples, the optical signal quality can be measurement using a low-power optical sensor or using measurements from another optical scan (e.g., for detecting on-wrist condition, background heart rate, etc.). In some examples, temperature can be measured by a temperature sensor (not shown) of device 100, 200. In some examples, the measurement of the physiological sensors can be initiated and/or continued while the temperature is above a threshold (e.g., measurement may not be attempted at low temperature due to potentially low blood perfusion).

In some examples, the measurement of the physiological signals (at state 410) can begin with configuration of the optical sensor (e.g., setting light emitter and light detector parameters such as LED current and gain). In some such examples, the measurement of the physiological signals can be aborted when the optical sensor is unable to be configured.

In some examples, to further save power, the background SpO2 measurements can use fewer channels than for a non-background SpO2 measurement (e.g., a user-requested SpO2 measurement). In some examples, the number of channels can be dynamically selected based on user preference or battery level (e.g., fewer channels used when battery level is below a threshold or in a low-power mode). In some examples, a smaller number of channels can be used initially, but if the smaller number of channels turns out to be inadequate (e.g., unsuccessful measurement attempt, insufficient signal quality), then a larger number of channels (or all channels) can be enabled for subsequent measurement attempts (e.g., until the signal quality improves and permits dynamic adjustment in the opposite direction to use fewer channels).

In some examples, the timing criteria (e.g., at state 408) can be dynamically adjusted. For example, the first threshold period of the first timing criterion (e.g., minimum separation time after a successful measurement) can be dynamically set based on time of day (e.g., greater separation at night as compared with daytime), user preference and/or battery level (e.g., greater separation when battery level is below a threshold or in a low-power mode). Additionally or alternatively, in some examples, the second timing criterion (e.g., number of measurement attempts permissible per hour) can be dynamically set based on time of day (e.g., fewer measurement attempts permissible per hour at night as compared with daytime), user preference and/or battery level (e.g., fewer measurement attempts permissible per hour when battery level is below a threshold or in a low-power mode). In some examples, the frequency of background measurement can by dynamically adapted based on the measured SpO2 level. For example, an SpO2 estimate less than a threshold can trigger a confirmation measurement cycle (e.g., one or more additional measurements of physiological signals) to confirm whether the user is indeed experiencing a low SpO2 reading.

In some examples, the background measurement of physiological signals and computation of SpO2 estimates using the measured physiological signals, as discussed above, can be employed for monitoring SpO2 levels for the user of the wearable device. In some examples, the background measurements of physiological signals and computation of SpO2 estimates can be used to alert the user of regarding one or more low SpO2 readings (e.g., if an SpO2 reading falls below a threshold). For example, a threshold number of low SpO2 measurements (e.g., two, three, four, five, six, seven, etc. SpO2 measurements falling below an 85%, 88%, 90%, 92%, 95%, etc. oxygen saturation level) for a period of time without intervening normal SpO2 measurements (e.g., one or more measurements above a threshold) may indicate that the user is experiencing sustained low SpO2 readings. Thus, the above described systems and processes can be utilized to alert the user to detection of low oxygen saturation levels, which may facilitate discovery that low oxygen saturation levels have been detected, and/or may encourage the user to seek appropriate medical attention, as discussed below.

Figure 8:
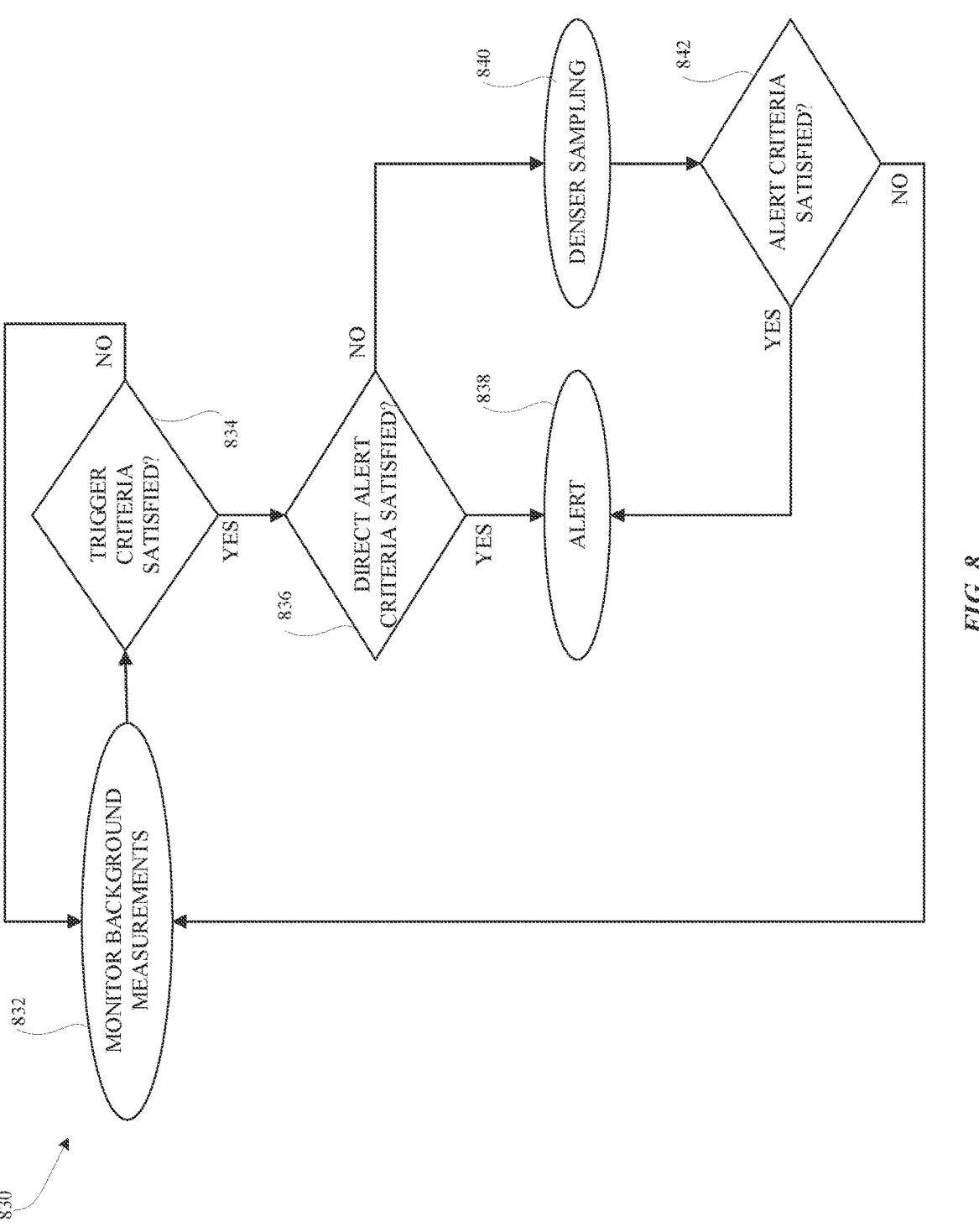
FIG. 8 illustrates an example state diagram for monitoring physiological signals using background measurement at different sampling rates and for alerting a user to regarding peripheral oxygen saturation according to examples of the disclosure.

FIG. 8 illustrates an example state diagram 830 for monitoring physiological signals using background measurement at different sampling rates (e.g., background estimation of peripheral oxygen saturation) and for alerting a user to regarding SpO2 readings (e.g., a notification that one or more SpO2 reading falls below a threshold) according to examples of the disclosure. State diagram 830 includes states 832, 834, 836, 838, 840 and 842. In some examples, state diagram 830 can define one or more criteria to satisfy to determine an operating mode for the background measurement by the optical sensor. For example, the optical sensor can operate in a first mode in which background measurements of physiological signals occur at a first sampling rate (e.g., as dictated by spacing in time of the measurements and/or by capping the number of measurements in a given period of time, such as measurements per hour) or can operated in a second mode in which background measurements of physiological signals occur at a second sampling rate, higher than the first sampling rate (e.g., as dictated by reduced spacing in time of the measurements relative to the first mode and/or by having a higher cap on the number of measurements in a given period of time compared with the first mode). In some examples, state diagram 830 can define one or more criteria to satisfy in order to generate an alert (e.g., an alert warning the user of the sustained low SpO2 readings or an alert to the user to initiate one or more subsequent measurements of physiological signals by an optical sensor). In some examples, the one or more alert criteria can include different criteria depending on the mode of operation of the optical sensor. For example, state diagram 830 includes trigger criteria and direct alert criteria that, when satisfied while in the first mode of operation of the optical sensor, can cause an alert to be issued. Additionally, state diagram 830 includes alert criteria for the second mode of operation of the optical sensor. In some examples, state diagram 830 can provide conditions for successful, power-efficient background estimation of SpO2 (e.g., with a relatively high likelihood of generating a physiologically valid estimate of SpO2, and with a higher sampling rate as the likelihood of sustained low SpO2 rises) and/or accurate generation of an alert based on detecting a plurality of low estimates of SpO2 (e.g., a threshold number of low SpO2 estimates with a false positive alert rate below a threshold, such as less than 0.1%, 0.25%, 0.5%, 0.75%, 1%, etc.), as discussed below.

State 832 can represent a first state to perform the background measurement of physiological signals using the optical sensor at a first sampling rate. The background measurements at state 832 can correspond to state diagram 400 in FIG. 4 (e.g., in which a first measurements are taken after satisfying the on-wrist criterion (e.g., state 402), settling time criterion (e.g., state 404), motion and/or posture criteria (e.g., state 406), and one or more timing criteria (e.g., state 408), and subsequent measurements are taken after satisfying the additional motion criterion (e.g., state 412), motion and/or posture criteria (e.g., state 406), and one or more timing criteria (e.g., state 408)). It should be understood that, in some examples, each and/or any combination of the processes described with reference to FIGS. 4-7 may be performed at state 832 to measure physiological signals using the optical sensor and calculate corresponding SpO2 measurements to monitor the user's oxygen saturation level.

In some examples, when a SpO2 estimate is generated based on a measurement at state 832, or when a low SpO2 or intermediate SpO2 estimate is detected by the device (e.g., when an SpO2 estimate falls below a first oxygen saturation threshold or between a first oxygen saturation threshold and a second oxygen saturation threshold, respectively), the system can transition to state 834. In some examples, the transition to state 834 can require a low SpO2 estimate (e.g., a borderline or nominal SpO2 estimate would not trigger a transition). In some examples, a first oxygen saturation threshold for an SpO2 estimate to be considered "low" can be in a range between 85-93% (e.g., an oxygen saturation threshold of 85%, 88%, 90%, 92%). In some examples, a second oxygen saturation threshold for an SpO2 estimate to be considered "intermediate" or "borderline" can be in a range between 87-95% (e.g., an oxygen saturation threshold of 87%, 90%, 92%, 92%, 94%). In some examples, the second oxygen saturation threshold includes a percent margin (e.g., 1%, 2%, 3%, 5%, etc.) above the first oxygen saturation threshold. In some examples, when a nominal or intermediate SpO2 estimate is generated based on a measurement at state 832, the state diagram remains in state 832.

State 834 can represent a second state to detect whether trigger criteria are satisfied (e.g., after computing a low SpO2 estimate using physiological signals measured using the optical sensor). In some examples, the trigger criteria include a measurement criterion that is satisfied when a first threshold number or greater than the threshold number of SpO2 estimates (e.g., 2 SpO2 estimates, 3 SpO2 estimates, 4 SpO2 estimates, etc.) falls below the oxygen saturation threshold (e.g., the first oxygen saturation threshold). In some examples, the trigger criteria also include a timing criterion that is satisfied when the first threshold number or greater than the threshold number of SpO2 estimates falls below the first oxygen saturation threshold across and/or within a threshold period of time. For example, the measurement criterion and timing criterion can be satisfied when a plurality (e.g., threshold number or greater) of low SpO2 estimates are measured across a first threshold period (e.g., 1 hour, 2, hours, 4, hours, 6 hours, 12 hours, 24 hours, etc.). In some examples, the measurement criterion and timing criterion can be satisfied when the plurality of low SpO2 estimates are measured within a second threshold period longer than the first threshold period (e.g., 6 hours, 10 hours, 12 hours, 18 hours, 24 hours, 36 hours, etc.). The second threshold period can avoid triggering a higher sampling rate and/or an alert where low SpO2 estimates are too separated in time to be reliably indicative of sustained low SpO2 readings. In some examples, the trigger criteria also include a second measurement criterion that is satisfied when, within the first threshold period of time, no SpO2 estimates (or less than a threshold number of SpO2 estimates) are measured above the second oxygen saturation threshold between subthreshold measurements (e.g., low SpO2 estimates). For example, the second measurement criterion is not satisfied if, after detecting the initial low SpO2 estimate at state 834 above, a second SpO2 estimate is measured above the second oxygen saturation threshold, and a third SpO2 estimate is measured below the first oxygen saturation threshold across the first threshold period of time (and optionally within the second threshold period of time). In some examples, an intermediate or borderline SpO2 estimate that falls between the first oxygen saturation threshold and the second oxygen saturation threshold (e.g., and does not exceed the second oxygen saturation threshold) does not play a role in the evaluation of the trigger criteria at state 834 (e.g., neither qualifying as a low SpO2 measurement or as an intervening nominal SpO2 measurement). In some examples, the measurement and timing criteria must all be satisfied for the trigger criteria to be satisfied. The trigger criteria can allow for mitigation of the effects of SpO2 estimate outliers and/or false positives that could prematurely initiate a higher sampling rate and or the alert generation process.

The system can transition from state 834 to state 836 upon the trigger criteria being satisfied. As shown in FIG. 8, if the trigger criteria are not satisfied (e.g., if some or all of the trigger criteria are not satisfied), the system can transition from state 834 back to state 832 and resume background measurements.

State 836 can represent a third state to detect whether one or more direct alert criteria are satisfied. In some examples, the direct alert criteria can include an alert criterion that is satisfied when a second threshold number (or greater than the second threshold number) of SpO2 estimates, greater than the first threshold number of SpO2 estimates, falls below the first oxygen saturation threshold (e.g., 4, 5, 6, 7, etc. SpO2 estimates fall below the first oxygen saturation threshold). For example, during the first threshold period of time described above with respect to the trigger criteria, the device may detect more than the first threshold number of low SpO2 estimates needed to satisfy the trigger criteria. In some examples, if the number of detected low SpO2 estimates reaches and/or exceeds the second threshold number of SpO2 estimates at state 836, the alert criterion is satisfied, which optionally satisfies the direct alert criteria. The system can transition from state 836 to state 838 when the direct alert criteria are satisfied, at which point the system will generate an alert notifying the user that low oxygen saturation levels have been detected. In some examples, if the number of detected low SpO2 estimates at state 836 does not reach the second threshold number of SpO2 estimates, the alert criterion is not satisfied, and thus the direct alert criteria are not satisfied. The system can transition from state 836 to state 840 when the direct alert criteria are not satisfied. In some examples, the second threshold number can be tuned to optimize between decreasing false positive alerts and reducing false negatives (without triggering the higher-sampling mode for the optical sensor).

State 840 can represent a fourth state to perform additional measurements of physiological signals using the optical sensor to determine whether low oxygen saturation levels are detected. For example, at state 840, a second plurality of physiological signals may be measured at a second sampling rate, greater than the first sampling rate, (e.g., at a denser sampling rate) to compute additional SpO2 estimates for monitoring the oxygen saturation level of the user. State 840 can correspond to the second mode of the optical sensor as described herein. In some examples, in the second mode of the optical sensor, one or more criteria may need to be satisfied for the optical sensor to perform a measurement. For example, one or more motion and/or posture criteria may need to be satisfied for the additional measurement for SpO2 estimates to be measured at state 840. These criteria, however, may be the same or different in the second mode than in the first mode (e.g., described with reference to FIG. 4). For example, measurements by the optical sensor may still be more likely to produce a valid and accurate SpO2 estimate while the user/device are stationary. Additionally or alternatively, the measurements by the optical sensor may be more likely to produce a valid and accurate SpO2 estimate while in certain postures (or while not in certain postures). Thus, while the system remains in state 840, measurements for use in SpO2 estimates may be performed when the one or more motion and/or posture criteria are satisfied (e.g., while the user is in supported posture (or not in unsupported postures) and while motion less than a threshold amount of motion for a threshold period of time, such as for 20 seconds, 30 seconds, 45 seconds, etc.)). In some examples, the motion and/or posture criteria can be relaxed in the second mode relative to the first mode such that a different motion threshold or threshold period of time may be used to allow for a measurement in the second mode.

In some examples, one or more timing criteria must be satisfied for the measurements to be performed at state 840. For example, background measurements by the optical sensor in the first mode may require a first threshold period of time between successful measurements (e.g., between 10 minutes and 120 minutes, between 15 minutes and 90 minutes, between 20 minutes and 60 minutes, etc.) to reduce the correlation between SpO2 measurements and/or to the power consumption of background sensing. Similarly, in a second mode, the measurements may be spaced apart such that a threshold period of time must elapse after a previous measurement to estimate of SpO2 before attempting a new measurement to estimate of SpO2. In some examples, in the second mode, the threshold period of time can be shorter than in the first mode (e.g., 1-20 minutes, 5-10 minutes, etc.). In some examples, the system can transition from state 840 to state 842 after each measurement of the second plurality of physiological signals/estimate of SpO2 in the second mode or optionally after each measurement of the second plurality of physiological signals with a low SpO2.

State 842 can represent a fifth state to detect whether alert criteria are satisfied while in the second mode of operation of the optical sensor and/or to detect whether to terminate the second mode. As discussed above, throughout states 832, 834, 836 and 840, a plurality of SpO2 estimates can be computed based on pluralities of physiological signals measured using the optical sensor. The alert criteria while operating the optical sensor in the second mode can include can include the alert criterion mentioned with respect to state 836 that is satisfied when a second threshold number of SpO2 estimates, greater than the first threshold number of SpO2 estimates, falls below the first oxygen saturation threshold. In some examples, the second threshold number in state 842 can be the same as in state 836. In some examples, the second threshold number in state 842 can be greater than the second threshold number in state 836. At state 842, if a total number of the SpO2 estimates that fall below the first oxygen saturation threshold measured during the first mode at state 832 to satisfy the trigger criteria (at state 834) and measured during the second mode using the denser sampling at state 840, reaches and/or exceeds the second threshold number of SpO2 estimates, the alert criteria is satisfied. The system can transition from state 842 to state 838 when the alert criteria are satisfied (e.g., when the second threshold number of SpO2 estimates falls below the first oxygen saturation threshold). When the total number of the SpO2 estimates that fall below the first oxygen saturation threshold measured during the first mode and during the second mode, to not reach or exceed the second threshold number of SpO2 estimates, the system can either transition back to the first mode as shown in FIG. 8 or return to dense sampling at state 840. In some examples, the alert criteria can include one or more termination criteria for exiting the second mode corresponding to the denser sampling at state 840 without an alert. In some examples, the one or more termination criteria are satisfied when one (or a threshold number) of the SpO2 estimates in the second mode exceeds the second oxygen saturation level (e.g., a nominal SpO2 reading). In some examples, the one or more termination criteria are satisfied when a threshold number (e.g., 2, 3, 5, etc.) of consecutive attempts at measuring physiological signals are unsuccessful (e.g., due to sudden movement of the device that does not satisfy the one or more motion and/or posture criteria) and no reliable SpO2 estimate(s) can be computed. In some examples, the one or more termination criteria are satisfied when at least a second threshold period of time (e.g., 20 minutes, 25 minutes, 30 minutes, 35 minutes, etc.) has elapsed since a prior successful SpO2 measurement (e.g., due to sustained motion of the device that does not satisfy the one or more motion and/or posture criteria). The system can transition from state 842 back to state 832 upon the one or more termination criteria being satisfied, as discussed in detail with reference to FIG. 9.

State 838 can represent a sixth state to generate an alert notifying the user that low oxygen saturation levels have been detected by the device. For example, generating the alert may include generating a notification corresponding to the alert for display via a display of the device. In some examples, generating the alert may include providing one or more visual indicators corresponding to the alert using one or more light emitters of the device (e.g., flashing one or more LEDs in a predefined pattern). In some examples, generating the alert may include providing one or more audio indicators corresponding to the alert using one or more speakers of the device (e.g., emitting a ring or tone, or providing an audio message corresponding to the alert). In some examples, generating the alert may include providing haptic feedback corresponding to the alert (e.g., causing a vibration or other physical sensation detectable on the wrist of the user). In some examples, generating the alert may include notifying a health care provider for the user if the user of the device authorizes the device to communicate with the health care provider (e.g., sending a notification, message, email, etc. to the user's doctor, medical team, family member, caretaker). Although not shown, in some examples, the system can transition from state 838 back to state 832 after issuing the alert (or after a threshold period has passed since issuing the alert and/or after user input is received directed to the alert).

It is understood that state diagram 800 can be performed at an electronic device such as device 100 or 200 (e.g., by processor 210 and/or by signal processor 214, or in any other circuitry configured to implement a state machine). It should be understood that the particular order of the description of the operations in the state diagram is merely exemplary and is not intended to indicate that the described order is the only order in which the operations could be performed. One of ordinary skill in the art would recognize various ways to reorder the operations described herein (e.g., some operations of state diagram 400 can be combined, reordered and/or omitted). In some examples, states 834 and 836 can be combined or reordered.

Figure 9:
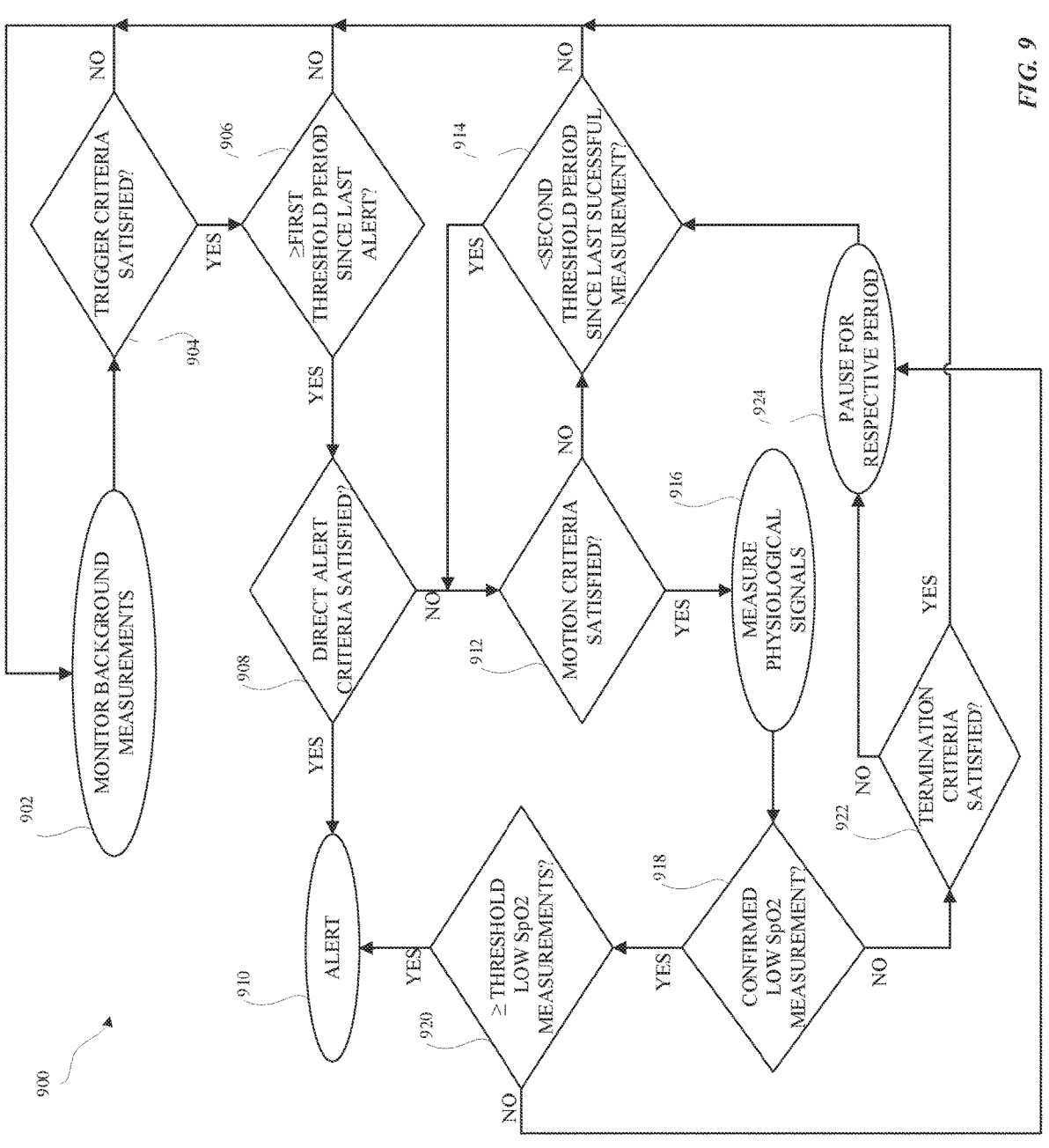
FIG. 9 illustrates an example process for monitoring physiological signals using background measurement at different sampling rates and for alerting a user to regarding peripheral oxygen saturation levels according to examples of the disclosure.

FIG. 9 illustrates an example flow chart or process 900 for monitoring physiological signals using background measurement at different sampling rates (e.g., background estimation of peripheral oxygen saturation) and for alerting a user to regarding low oxygen saturation levels according to examples of the disclosure. Flow chart or process 900 can be viewed as a more detailed state diagram than the state diagram 800 of FIG. 8.

As shown in FIG. 9, process 900 may begin at 902 with the monitoring of background SpO2 measurements in a first mode of operation. In some examples, in the first mode of operation, a first plurality of physiological signals may be measured by the device at a first sampling rate using the optical sensor, as described herein with respect to first state 832 of FIG. 8 and with respect to FIG. 4, to compute a first plurality of SpO2 estimates. When the device detects an SpO2 estimate that falls below the first SpO2 estimate threshold (e.g., a low oxygen saturation level), the system may evaluate whether the trigger criteria have been satisfied (e.g., as described with respect to state 834). As discussed above, the trigger criteria ("trigger criteria," "first criteria") optionally includes a criterion that is satisfied when a first threshold number of SpO2 estimates (e.g., 2, 3, 4, etc. estimates) fall below the first SpO2 threshold. As shown, if the criterion is not satisfied because the first threshold number of SpO2 estimates that fall below the first SpO2 threshold has not been detected, the system can transition back to continue monitoring SpO2 measurements at the first sampling rate at 902. In some examples, if the trigger criteria are satisfied at 904, the system may evaluate whether at least a threshold period of time has elapsed since the generation of a previous alert, at 906. For example, to improve the user experience (e.g., reduce frequency of repetitive alerts) and to reduce power consumption, the system can avoid generating an alert and maintain operation of the optical sensor in the first mode for the threshold period of time. For example, if less than the threshold period of time (e.g., 20 minutes, 25 minutes, 30 minutes, 35 minutes, 45 minutes, 1 hour, etc.) has elapsed since the generation of a previous alert (e.g., at state 838 or at 910), the system can continue monitoring SpO2 measurements at the first sampling rate at 902. In some examples, if at least the threshold period of time has elapsed since the generation of a previous alert, the system can evaluate whether the direct alert criteria are satisfied at 908. As discussed above, the direct alert criteria can be satisfied when at least a second threshold number of low SpO2 estimates, greater than the first threshold number of low SpO2 estimates, are detected by the device (e.g., as described with respect to state 836). For example, if a total number of SpO2 estimates falling below the first SpO2 estimate threshold meets or exceeds the second threshold number of SpO2 estimates, the system can issue an alert (e.g., a notification, haptic feedback, a message, etc.), at step 910 (e.g., as described with reference to state 838). In some examples, if the total number of SpO2 estimates falling below the first SpO2 estimate threshold does not meet the second threshold number of SpO2 estimates, the system can cause the optical sensor to operate in the second mode instead of the first mode (e.g., corresponding to a transition to state 840).

As discussed above, in the second mode the optical sensor can operate with a denser sampling rate in which additional physiological signals (e.g., a second plurality of physiological signals) are measured to compute additional SpO2 estimate data for oxygen saturation level analysis. In some examples, in the second mode, the system can use second criteria to evaluate whether to remain in the second mode and can use third criteria to evaluate whether to issue an alert. For example, at 912, the system can evaluate whether one or more motion criteria and/or one or more posture criteria are satisfied (e.g., as described with reference to state 840 and motion and/or posture criteria of state 406). For example, measurements by the optical sensor may be more likely to produce a valid and accurate SpO2 estimate while the user/device are stationary (e.g., motion less than a threshold). Additionally or alternatively, the measurements by the optical sensor may be more likely to produce a valid and accurate SpO2 estimate while in certain postures (or while not in certain postures). In some examples, if the one or more motion/posture criteria are satisfied, the system performs a measurement using the optical sensor for use in estimating SpO2 at 916. In some examples, if the one or more motion/posture criteria are not satisfied at 912, the system can evaluate whether less than a second threshold period of time has elapsed since a prior successful SpO2 measurement (e.g., a timing criterion). For example, if less than the second threshold period of time (e.g., 20 minutes, 25 minutes, 30 minutes, 35 minutes, etc.) has elapsed since a prior successful SpO2 measurement (e.g., computation of a reliable SpO2 estimate), the system can again evaluate the one or more motion/posture criteria at 912 (e.g., in an attempt to satisfy conditions for another measurement). Effectively, if the second threshold period of time is not exceeded between successive successful SpO2 measurements, the system can continue to attempt to satisfy conditions for another measurement at 912 until the one or more motion and/or posture criteria are satisfied or the second threshold period of time elapses. In some examples, if the second threshold period of time is exceeded, the system can transition back to background sampling of physiological signal measurements in the first mode of the optical sensor (e.g., returning to state 832 or 902). Thus, the elapsing of the second threshold period of time in the second mode of operation of the optical sensor can be one way to satisfy one or more second criteria to transition from the second mode of operation to the first mode of operation of the optical sensor (e.g., a termination of the denser sampling of the second mode). This termination of the denser sampling of the second mode can save power of the device when the denser measurement attempts are not successful.

As described herein, in the second mode of operation, the device may operate at a higher sampling rate to provide a second plurality of SpO2 estimates more rapidly. The second plurality of SpO2 measurements can be used as confirmation measurements to increase the likelihood of detecting low oxygen saturation levels accurately if the user is indeed experiencing low oxygen saturation levels. As shown in FIG. 9, the system may perform a confirmation evaluation at 918 for a measurement of the physiological signal by the optical sensor in the second mode to evaluate whether the SpO2 estimate for the measurement at 916 falls below the first SpO2 estimate threshold. If the SpO2 estimate falls below the first SpO2 estimate threshold, the detection of low SpO2 measurements is confirmed, and the system can then evaluate whether one or more alert criteria are satisfied (e.g., as described with reference to state 842). If the SpO2 estimate at does not fall below the first SpO2 threshold (or if the measurement at 916 was unsuccessful), the system may evaluate whether to remain in the second mode at 922.

In some examples, the one or more second criteria can include the one or more termination criteria at 922. As shown in FIG. 9, at 922, the system may evaluate whether the one or more termination criteria are satisfied. In some examples, the one or more termination criteria can be satisfied when one (or a threshold number) of the additional SpO2 estimates exceeds the second oxygen saturation level (e.g., a nominal SpO2 reading). In some examples, the one or more termination criteria can alternatively be satisfied when a threshold number (e.g., 2, 3, etc.) consecutive attempts at measuring physiological signals at 916 are unsuccessful (e.g., due to sudden movement of the device that does not satisfy the one or more motion and/or posture criteria, due to insufficient or unreliable/noisy data, etc.) and no accurate/qualifying SpO2 estimate(s) can be computed. In some examples, the one or more termination criteria can be satisfied when at least a second threshold period of time (e.g., 20 minutes, 25 minutes, 30 minutes, 35 minutes, etc.) has elapsed since a prior successful SpO2 measurement (e.g., due to sustained motion of the device that does not satisfy the one or more motion and/or posture criteria) as described similarly with respect to 914. If the one or more termination criteria are satisfied, the system can transition from the second mode of operation to the first mode of operation for the optical sensor (e.g., return to performing background measurements at the first sampling rate at 902/state 832). If the one or more termination criteria are not satisfied, the system does not transition out of the second mode (e.g., remains in the second mode to perform more measurements at the higher sampling rate).

For example, when the system remains in the second mode at 922, the system can, in some examples, pause for a respective period of time (e.g., 2 minutes, 5 minutes, 8 minutes, 10 minutes, etc.) before another measurement can be performed by the optical sensor (e.g., returning to 914 or 912). For example, background measurements by the optical sensor in the second mode may be spaced apart such that a threshold period of time must elapse after a successful estimate of SpO2 before attempting a new estimate of SpO2 to reduce the correlation between SpO2 measurements and/ or to reduce the power consumption of background sensing.

Referring back to evaluation at 918 of FIG. 9, if the SpO2 estimate from the measurement at 916 confirms detection of low oxygen saturation levels, the system may evaluate whether one or more third criteria are satisfied for issuing an alert. For example, the one or more third criteria may include a criterion that is satisfied when at least a second threshold number of SpO2 estimates falls below the first SpO2 estimate threshold without termination of the second mode (e.g., without intervening nominal SpO2 readings and while the optical sensor is able to generate successful measurements to remain in the second mode). In some examples, the evaluation at 920 considers the total number of low SpO2 estimates from measurements of the optical sensor in the first mode and the second mode. For example, the total number can include low SpO2 estimates used to satisfy the trigger criteria and the low SpO2 estimates from measurements of the optical sensors in the second mode. If at least a second threshold number of the total number of SpO2 estimates that fall below the first SpO2 estimate threshold are detected, the system can transitions issue an alert at 910 (e.g., as described with reference to state 838). For example, as discussed above with reference to FIG. 8, the system/ device may generate a notification, provide a visual indica-tor, provide an auditory indicator, provide haptic feedback, issue a warning to a health provider, among other possibili-ties. If less than a second threshold number of the total number of SpO2 estimates that fall below the first SpO2 estimate threshold are detected, the system can pause for the respective period of time at 924 and continue to attempt confirmatory measurement in the second mode of operation.

Following the issuance of the alert at 910, the system may transition from the second mode of operation back to the first mode of operation (e.g., transition back to background measurements at the first sampling rate at 902/state 832). In some examples, the system/device transitions from the sec-ond mode to the first mode after a threshold period of time elapses after issuance of the alert (e.g., 1-5 minutes, etc.). In some examples, the system transitions back to the first mode of operation in response to detecting user input directed to the issued alert (e.g., user acknowledgement or dismissal of the alert). For example, the system/device can optionally transition from the second mode to the first mode in response to detecting a selection (e.g., tap, touch, swipe, etc.) of the notification displayed on the display of the device. In another example, the system/device can transition from the second mode to the first mode in response to actuation of a button of the device.

It is understood that process 900 can be performed at an electronic device such as device 100 or 200 (e.g., by processor 210 and/or by signal processor 214). It should be understood that the particular order of the description of the operations in the diagram is merely exemplary and is not intended to indicate that the described order is the only order in which the operations could be performed. One of ordinary skill in the art would recognize various ways to reorder the operations described herein (e.g., some operations of pro-cess 900 can be combined, reordered and/or omitted). In some examples, process 900 is optionally performed in response to receiving a user-initiated request to measure physiological signals for monitoring of oxygen saturation levels.

Additionally, it is understood that although state diagram 800 and flowchart/process 900 refer only to background measurement of physiological signals to estimate SpO2, it is understood that user initiated measurements can also be considered. For example, an estimate of SpO2 initiated by user input (e.g., a user request to measure SpO2) can be counted for the number of SpO2 estimates to satisfy or not satisfy the trigger criteria (e.g., at state 834 or at 904) to satisfy or not satisfy direct alert criteria (e.g., at state 836 or at 908), to satisfy or not satisfy alert criteria in the second mode of operation of the optical sensor (at state 842 or at 920), or for evaluation of termination criteria (e.g., at state 842 or at 922). Additionally, although different sampling rates are described in a first mode and a second mode, it is understood that, in some examples, the optical sensor can operate using the sampling rate rather than different sampling rates (though it may take longer to satisfy the alert criteria, in some examples).

Figure 10A:
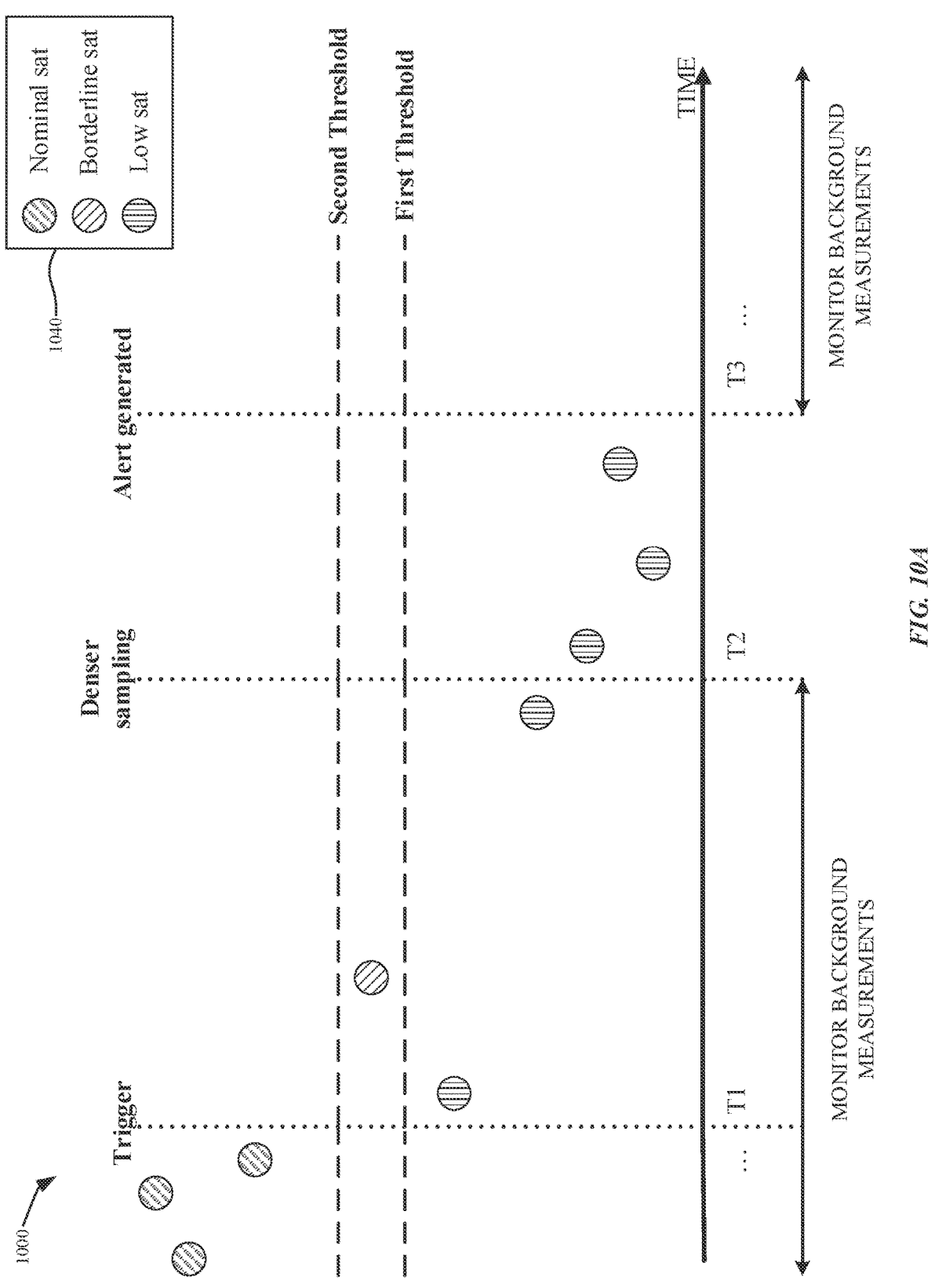
FIGS. 10A-10B illustrate timing diagrams of example operation of a state diagram of FIG. 8 or process of FIG. 9 according to examples of the disclosure.
Figure 10B:
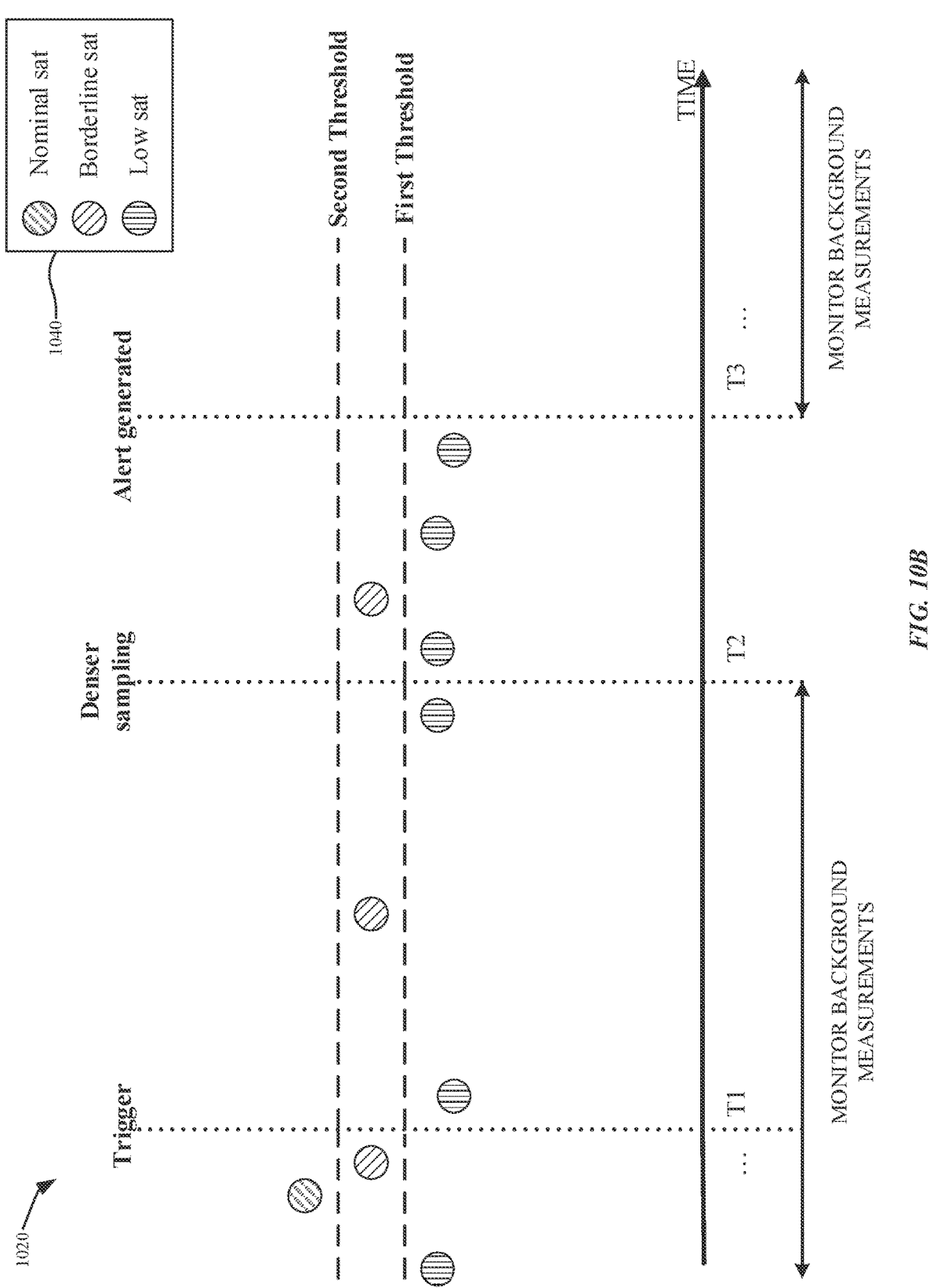

FIGS. 10A-10B illustrate timing diagrams of example operation of a state diagram of FIG. 8 or process of FIG. 9 according to examples of the disclosure. Timing diagram 1000 corresponds to an alert for low oxygen generated for a true positive example, and timing diagram 1020 corresponds to an alert for low oxygen generated for a borderline example. A true positive example can refer to an instance in which the true SpO2 measurements fall well below the first SpO2 estimate threshold, whereas a borderline example can refer to an instance in which the true SpO2 measurements may sometimes fall below the first SpO2 estimate threshold and/or between the first SpO2 estimate threshold and the second SpO2 estimate threshold, but remain within a threshold amount of the first SpO2 estimate (e.g., borderline SpO2 measurements or low SpO2 measurements within 1-2% SpO2 of the first SpO2 estimate threshold). Reference will be made to nominal saturation estimates (nominal SpO2), borderline saturation estimates (borderline SpO2), and low saturation estimates (low SpO2), as indicated by legend 1040. A nominal saturation estimate refers to an SpO2 estimate that is detected above the second SpO2 estimate threshold. A borderline saturation estimate refers to an SpO2 estimate that is detected between the first SpO2 estimate threshold and the second SpO2 estimate threshold. A low saturation estimate refers to an SpO2 estimate that is detected below the first SpO2 estimate threshold. In the examples of FIGS. 10A-10B, the alert is issued upon detecting at least five total low saturation estimates including at least two while the optical sensor operates in the first mode and at least three while the optical sensor operates in the second mode.

In timing diagram 1000 of FIG. 10A, prior to T1, the system is optionally monitoring background estimates of SpO2 in the first mode (e.g., state 832 of FIG. 8). As shown, in the time prior to T1, the system/device detects a plurality of SpO2 estimates including three illustrated nominal saturation estimates (e.g., above the second SpO2 estimate threshold). At T1, the system detects a low saturation estimate which falls below the first SpO2 estimate threshold. Between T1 and T2, the system detects additional SpO2 estimates, including a borderline saturation estimate and at least one additional low saturation estimate. As shown, the trigger criteria (of state 834) can be satisfied when the period between T1 and T2 satisfies the one or more timing criteria, and when the threshold number of low saturation estimates are detected without detecting a nominal saturation estimate. As described herein, the detection of the borderline saturation estimate between T1-T2 does not cause contribute to the threshold number of low saturation estimate or nominal saturation estimates, and thereby does not trigger or reset the criteria (e.g., like a nominal saturation estimate would). At T2, with the threshold number of low saturation estimates having been detected, the system can transition to the second mode of operation for the optical sensor (e.g., state 840) because fewer than the second threshold number of low saturation estimates have been detected (e.g., corresponding to the evaluation at state 836 without satisfying the one or more direct alert criteria).

Between T2 and T3, in the second mode, the system estimates SpO2 using measurements by the optical sensor at the denser sampling state. FIG. 10A illustrates, from T2-T3, the system detecting three additional low saturation estimates, without satisfaction of the one or more termination criteria (e.g., detecting a nominal saturation estimate, etc.). The at least three additional low saturation estimates bring the total number of low saturation estimates to at least five between T1 and T3, which thus satisfies the alert criteria for the second mode (e.g., at state 842 at 920). As a result, the system can issue the alert at T3, and return to continue monitoring the background estimates of SpO2 in the first mode.

In timing diagram 1020 of FIG. 10B, like in FIG. 10A, the system can operate the optical sensor in the first mode until T2 and after T3 and operate the optical sensor in the second mode before T2 and T3. Prior to T1, FIG. 10B illustrates three SpO2 measurements including one low saturation estimate, one nominal saturation estimate, and one borderline saturation estimate. The nominal saturation estimate can disqualify the first low saturation estimate from contributing to satisfying the trigger criteria. From T1 to T2, FIG. 10B shows similar behavior to FIG. 10A, but with a low saturation estimate closer to borderline than its counterpart in FIG. 10A, and as a result, at T2, the system transitions to operate the optical sensor in the second mode at a higher sampling rate. From T2 to T3, FIG. 10B shows similar behavior to FIG. 10A, but with a low saturation estimates closer to borderline than their counterparts in FIG. 10A and one borderline saturation estimate. The detection of the borderline saturation estimate from T2-T3 does not cause the one or more termination criteria to be satisfied. As a result of detecting the threshold number of low saturation estimates from T1-T3, at T3, the system can issue the alert at T3, and return to continue monitoring the background estimates of SpO2 in the first mode.

It is understood that the timing diagrams of FIGS. 10A-10B are examples and that numerous alternative illustrations for showcasing the timing of state diagram 800 of FIG. 8 are possible.

As discussed above, aspects in of the present technology include the gathering and use of physiological information. The technology may be implemented along with technologies that involve gathering personal data that relates to the user's health and/or uniquely identifies or can be used to contact or locate a specific person. Such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information, such as data generated and used by the present technology, can be used to the benefit of users. For example, monitoring physiological characteristics, such SpO2, may allow a user to track or otherwise gain insights about their health.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a wearable device. The wearable device can comprise: an optical sensor including a plurality of channels and configured to measure physiological signals from the plurality of channels; and a processor coupled to the optical sensor. The processor can be programmed to: in accordance with a determination that one or more first criteria are satisfied, the one or more first criteria including a motion criterion that is satisfied when a measure of motion is less than a motion threshold: measure first physiological signals using the optical sensor; and process the first physiological signals to compute an SpO2 estimate using the first physiological signals. Additionally or alternatively to one or more of the examples disclosed above, in some examples, the processor can be further programmed to: in accordance with a determination that one or more first criteria are not satisfied: forgo measuring the first physiological signals; and forgo processing the first physiological signals to compute the SpO2 estimate. Additionally or alternatively to one or more of the examples disclosed above, in some examples, the one or more first criteria can further include a posture criterion that is satisfied when predetermined postures are excluded based on motion data. Additionally or alternatively to one or more of the examples disclosed above, in some examples, the one or more first criteria can further include an on-wrist criterion that is satisfied when the optical sensor is detected in proximity to or contact with a user's tissue. Additionally or alternatively to one or more of the examples disclosed above, in some examples, the one or more first criteria can further include a settling criterion that is satisfied a first threshold period of time after satisfying the on-wrist criterion. Additionally or alternatively to one or more of the examples disclosed above, in some examples, the one or more first criteria can further include a first timing criterion that is satisfied when a second threshold period of time has passed since a prior measurement of the physiological signals by the optical sensor to compute a prior SpO2 estimate. Additionally or alternatively to one or more of the examples disclosed above, in some examples, the one or more first criteria can further include a second timing criterion that is satisfied when fewer than a threshold number of prior measurement of the physiological signals by the optical sensor have been performing within a third threshold period of time. Additionally or alternatively to one or more of the examples disclosed above, in some examples, measuring the first physiological signals using the optical sensor can include measuring data for a plurality of windows, including a first window of first data from the plurality of channels, a second window of second data from the plurality of channels. Additionally or alternatively to one or more of the examples disclosed above, in some examples, the first window and the second window partially overlap. Additionally or alternatively to one or more of the examples disclosed above, in some examples, processing the first physiological signals to compute the SpO2 estimate using the first physiological signals can comprise: computing a plurality of window SpO2 estimates, each of the plurality of window SpO2 estimates computed using the data corresponding to one of the plurality of windows; and computing the SpO2 estimate using the plurality of window SpO2 estimates. Additionally or alternatively to one or more of the examples disclosed above, in some examples, the processor can be further programmed to: in accordance with a determination that one or more second criteria are satisfied, the second criteria including a motion criterion that is satisfied when the measure of motion is greater than a threshold for a threshold period of time after measuring the first physiological signals: measure second physiological signals using the optical sensor; and process the second physiological signals to compute an second SpO2 estimate using the second physiological signals. Additionally or alternatively to one or more of the examples disclosed above, in some examples, the processor can be programmed to measure and process the first physiological signals without user intervention. Additionally or alternatively to one or more of the examples disclosed above, in some examples, the processor can be further programmed to: in accordance with a determination that one or more termination criteria are satisfied while measuring the first physiological signals using the optical sensor, cease measuring the first physiological signals; and in accordance with a determination that one or more termination criteria are not satisfied while measuring the first physiological signals using the optical sensor, continue measuring at least a portion of the first physiological signals. Additionally or alternatively to one or more of the examples disclosed above, in some examples, the termination criteria can include a motion criterion that is satisfied when the measure of motion is greater than the motion threshold. Additionally or alternatively to one or more of the examples disclosed above, in some examples, the termination criteria can include a motion criterion that is satisfied when the measure of motion is greater than the motion threshold for at least a portion of each window of the first physiological signals. Additionally or alternatively to one or more of the examples disclosed above, in some examples, the processor can be further programmed to: in accordance with a determination that one or more termination criteria are satisfied while measuring the first physiological signals using the optical sensor: in accordance with a determination that the first physiological signals measured before ceasing measuring the first physiological signals includes more than a threshold amount of data, compute the SpO2 estimate; and in accordance with a determination that the first physiological signals measured before ceasing measuring the first physiological signals includes less than the threshold amount of data, forgo computing the SpO2 estimate.

Some examples of the disclosure are directed to a method. The method can comprise: in accordance with a determination that one or more first criteria are satisfied, the one or more first criteria including a motion criterion that is satisfied when a measure of motion is less than a motion threshold: measuring first physiological signals using an optical sensor including a plurality of channels and configured to measure physiological signals from the plurality of channels; and processing the first physiological signals to compute an SpO2 estimate using the first physiological signals. Additionally or alternatively to one or more of the examples disclosed above, in some examples, the method can further comprise: in accordance with a determination that one or more first criteria are not satisfied: forgoing measuring the first physiological signals; and forgoing processing the first physiological signals to compute the SpO2 estimate. Additionally or alternatively to one or more of the examples disclosed above, in some examples, the one or more first criteria can further include a posture criterion that is satisfied when predetermined postures are excluded based on motion data. Additionally or alternatively to one or more of the examples disclosed above, in some examples, the one or more first criteria can further include an on-wrist criterion that is satisfied when the optical sensor is detected in proximity to or contact with a user's tissue. Additionally or alternatively to one or more of the examples disclosed above, in some examples, the one or more first criteria can further include a settling criterion that is satisfied a first threshold period of time after satisfying the on-wrist criterion. Additionally or alternatively to one or more of the examples disclosed above, in some examples, the one or more first criteria can further include a first timing criterion that is satisfied when a second threshold period of time has passed since a prior measurement of the physiological signals by the optical sensor to compute a prior SpO2 estimate. Additionally or alternatively to one or more of the examples disclosed above, in some examples, the one or more first criteria can further include a second timing criterion that is satisfied when fewer than a threshold number of prior measurement of the physiological signals by the optical sensor have been performing within a third threshold period of time. Additionally or alternatively to one or more of the examples disclosed above, in some examples, measuring the first physiological signals using the optical sensor can include measuring data for a plurality of windows, including a first window of first data from the plurality of channels, a second window of second data from the plurality of channels. Additionally or alternatively to one or more of the examples disclosed above, in some examples, the first window and the second window partially overlap. Additionally or alternatively to one or more of the examples disclosed above, in some examples, processing the first physiological signals to compute the SpO2 estimate using the first physiological signals can comprise: computing a plurality of window SpO2 estimates, each of the plurality of window SpO2 estimates computed using the data corresponding to one of the plurality of windows; and computing the SpO2 estimate using the plurality of window SpO2 estimates. Additionally or alternatively to one or more of the examples disclosed above, in some examples, the method can further comprise: in accordance with a determination that one or more second criteria are satisfied, the second criteria including a motion criterion that is satisfied when the measure of motion is greater than a threshold for a threshold period of time after measuring the first physiological signals: measuring second physiological signals using the optical sensor; and processing the second physiological signals to compute an second SpO2 estimate using the second physiological signals. Additionally or alternatively to one or more of the examples disclosed above, in some examples, measuring and processing the first physiological signals can be performed without user intervention. Additionally or alternatively to one or more of the examples disclosed above, in some examples, the method can further comprise: in accordance with a determination that one or more termination criteria are satisfied while measuring the first physiological signals using the optical sensor, ceasing measuring the first physiological signals; and in accordance with a determination that one or more termination criteria are not satisfied while measuring the first physiological signals using the optical sensor, continuing measuring at least a portion of the first physiological signals. Additionally or alternatively to one or more of the examples disclosed above, in some examples, the termination criteria can include a motion criterion that is satisfied when the measure of motion is greater than the motion threshold. Additionally or alternatively to one or more of the examples disclosed above, in some examples, the termination criteria can include a motion criterion that is satisfied when the measure of motion is greater than the motion threshold for at least a portion of each window of the first physiological signals. Additionally or alternatively to one or more of the examples disclosed above, in some examples, the method can further comprise: in accordance with a determination that one or more termination criteria are satisfied while measuring the first physiological signals using the optical sensor: in accordance with a determination that the first physiological signals measured before ceasing measuring the first physiological signals includes more than a threshold amount of data, computing the SpO2 estimate; and in accordance with a determination that the first physiological signals measured before ceasing measuring the first physiological signals includes less than the threshold amount of data, forgoing computing the SpO2 estimate.

Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Some examples of the disclosure are directed to a wearable device. The wearable device can comprise an optical sensor configured to measure physiological signals. The optical sensor can be configured to measure a first plurality of physiological signals at a first sampling rate in a first mode and can be configured to measure a second plurality of physiological signals at a second sampling rate, greater than the first sampling rate, in a second mode. The wearable device can comprise a processor coupled to the optical sensor. The processor can be programmed to: process the first plurality of physiological signals to compute a first plurality of SpO2 estimates using the first plurality of physiological signals, and process the second plurality of physiological signals to compute a second plurality of SpO2 estimates using the second plurality of physiological signals. The processor can be further programmed to, in the first mode: in accordance with a determination that one or more first criteria are satisfied, transition from the first mode to the second mode; and in accordance with a determination that the one or more first criteria are not satisfied, forgo transitioning from the first mode to the second mode. The one or more first criteria can include a criterion that is satisfied when a first threshold number of the first plurality of SpO2 estimates falls below a first SpO2 estimate threshold without an intervening one of the first plurality of estimates exceeding a second SpO2 estimate threshold. The processor can be further programmed to, in the second mode: in accordance with a determination that one or more second criteria are satisfied, transition from the second mode to the first mode; and in accordance with a determination that the one or more second criteria are not satisfied, forgo transitioning from the second mode to the first mode.

Additionally or alternatively to one or more of the examples disclosed above, in some examples, the processor may be further programmed to: in accordance with a determination that one or more third criteria are satisfied, generate an alert; and in accordance with a determination that the one or more third criteria are not satisfied, forgo generating the alert. Additionally or alternatively to one or more of the examples disclosed above, in some examples, the one or more third criteria can include: a timing criterion that is satisfied when at least a first threshold period of time has elapsed since a prior generation of the alert. Additionally or alternatively to one or more of the examples disclosed above, in some examples, the one or more third criteria can include: a criterion that is satisfied when, in the first mode, a second threshold number, greater than the first threshold number, of the first plurality of SpO2 estimates falls below the first SpO2 estimate threshold without the intervening one of the first plurality of estimates exceeding the second SpO2 estimate threshold; or a criterion that is satisfied when, in the second mode, a third threshold number, greater than the first threshold number, of the first plurality of SpO2 estimates and of the second plurality of SpO2 estimates falls below the first SpO2 estimate threshold, without an intervening one of the first plurality of estimates exceeding the second SpO2 estimate threshold.

Additionally or alternatively to one or more of the examples disclosed above, in some examples, generating the alert can include at least one of: generating a notification corresponding to the alert for display via a display of the wearable device; providing one or more visual indicators corresponding to the alert using one or more light emitters of the wearable device; providing one or more audio indicators corresponding to the alert using one or more speakers of the wearable device; providing haptic feedback corresponding to the alert; and in accordance with a determination that the wearable device is authorized to communicate with a health care provider for a user of the wearable device, notifying the health care provider.

Additionally or alternatively to one or more of the examples disclosed above, in some examples, measuring the second plurality of physiological signals at the second sampling rate in a second mode can comprise: in accordance with a determination that one or more fourth criteria are satisfied, measuring one of the second plurality of physiological signals using the optical sensor; and in accordance with a determination that the one or more fourth criteria are not satisfied, forgoing measuring the one of the second plurality of physiological signals using the optical sensor. Additionally or alternatively to one or more of the examples disclosed above, in some examples, the one or more fourth criteria can include: a motion criterion that is satisfied when a measure of motion is less than a motion threshold; and a timing criterion that is satisfied when less than a first threshold period of time has elapsed since a prior measurement of another of the second plurality of physiological signals by the optical sensor used to compute an SpO2 estimate. Additionally or alternatively to one or more of the examples disclosed above, in some examples, the one or more fourth criteria can include a posture criterion that is satisfied when predetermined postures are excluded based on motion data.

Additionally or alternatively, in some examples, the one or more second criteria can include: a criterion that is satisfied when a threshold period of time has elapsed since a qualifying prior measurement of the second physiological signals by the optical sensor used to compute an SpO2 estimate; or a criterion that is satisfied when a threshold number of the second plurality of SpO2 estimates exceeds the second SpO2 estimate threshold; or a criterion that is satisfied when a second threshold number, greater than the first threshold number, of the first plurality of SpO2 estimates and of the second plurality of SpO2 estimates falls below the first SpO2 estimate threshold, without an intervening one of the second plurality of estimates exceeding the second SpO2 estimate threshold.

Some examples of the disclosure are directed to a method. The method can comprise: measuring a first plurality of physiological signals at a first sampling rate in a first mode using an optical sensor of a wearable device; measuring a second plurality of physiological signals at a second sampling rate, greater than the first sampling rate, in a second mode using the optical sensor; processing, using a processor (e.g., processing circuitry), the first plurality of physiological signals to compute a first plurality of SpO2 estimates using the first plurality of physiological signals, and processing, using the processor, the second plurality of physiological signals to compute a second plurality of SpO2 estimates using the second plurality of physiological signals. The method can further comprise, in the first mode: in accordance with a determination that one or more first criteria are satisfied, the one or more first criteria including a criterion that is satisfied when a first threshold number of the first plurality of SpO2 estimates falls below a first SpO2 estimate threshold without an intervening one of the first plurality of estimates exceeding a second SpO2 estimate threshold, transitioning from the first mode to the second mode; and in accordance with a determination that the one or more first criteria are not satisfied, forgoing transitioning from the first mode to the second mode. The method can further comprise, in the second mode: in accordance with a determination that one or more second criteria are satisfied, transitioning from the second mode to the first mode; and in accordance with a determination that the one or more second criteria are not satisfied, forgoing transitioning from the second mode to the first mode.

Additionally or alternatively to one or more of the examples disclosed above, in some examples, the method can further comprise: in accordance with a determination that one or more third criteria are satisfied, generating an alert; and in accordance with a determination that the one or more third criteria are not satisfied, forgoing generating the alert. Additionally or alternatively to one or more of the examples disclosed above, in some examples, the one or more third criteria can include: a timing criterion that is satisfied when at least a first threshold period of time has elapsed since a prior generation of the alert. Additionally or alternatively to one or more of the examples disclosed above, in some examples, the one or more third criteria can include: a criterion that is satisfied when, in the first mode, a second threshold number, greater than the first threshold number, of the first plurality of SpO2 estimates falls below the first SpO2 estimate threshold without the intervening one of the first plurality of estimates exceeding the second SpO2 estimate threshold; or a criterion that is satisfied when, in the second mode, a third threshold number, greater than the first threshold number, of the first plurality of SpO2 estimates and of the second plurality of SpO2 estimates falls below the first SpO2 estimate threshold, without an intervening one of the first plurality of estimates exceeding the second SpO2 estimate threshold.

Additionally or alternatively to one or more of the examples disclosed above, in some examples, generating the alert can include at least one of: generating a notification corresponding to the alert for display via a display of the wearable device; providing one or more visual indicators corresponding to the alert using one or more light emitters of the wearable device; providing one or more audio indicators corresponding to the alert using one or more speakers of the wearable device; providing haptic feedback corresponding to the alert; and in accordance with a determination that the wearable device is authorized to communicate with a health care provider for a user of the wearable device, notifying the health care provider.

Additionally or alternatively to one or more of the examples disclosed above, in some examples, measuring the second plurality of physiological signals at the second sampling rate in a second mode can comprise: in accordance with a determination that one or more fourth criteria are satisfied, measuring one of the second plurality of physiological signals using the optical sensor; and in accordance with a determination that the one or more fourth criteria are not satisfied, forgoing measuring the one of the second plurality of physiological signals using the optical sensor. Additionally or alternatively to one or more of the examples disclosed above, in some examples, the one or more fourth criteria can include: a motion criterion that is satisfied when a measure of motion is less than a motion threshold; and a timing criterion that is satisfied when less than a first threshold period of time has elapsed since a prior measurement of another of the second plurality of physiological signals by the optical sensor used to compute an SpO2 estimate. Additionally or alternatively to one or more of the examples disclosed above, in some examples, the one or more fourth criteria can include a posture criterion that is satisfied when predetermined postures are excluded based on motion data.

Additionally or alternatively to one or more of the examples disclosed above, in some examples, the one or more second criteria can include: a criterion that is satisfied when a threshold period of time has elapsed since a qualifying prior measurement of the second physiological signals by the optical sensor used to compute an SpO2 estimate; or a criterion that is satisfied when a threshold number of the second plurality of SpO2 estimates exceeds the second SpO2 estimate threshold; or a criterion that is satisfied when a second threshold number, greater than the first threshold number, of the first plurality of SpO2 estimates and of the second plurality of SpO2 estimates falls below the first SpO2 estimate threshold, without an intervening one of the second plurality of estimates exceeding the second SpO2 estimate threshold.

Some examples of the disclosure are directed to a non-transitory computer readable storage medium. The non-transitory computer readable storage medium can store instructions, which when executed by an electronic device comprising processing circuitry, can cause the processing circuitry to perform any of the above methods.

Some examples of the disclosure are directed to a wearable device comprising an optical sensor configured to measure physiological signals and processing circuitry coupled to the optical sensor. The processing circuitry can be programmed to measure one or more physiological signals (e.g., at a first sampling rate and/or at a second sampling rate) using the optical sensor. The processing circuitry can be programmed to process the one or more physiological signals to compute one or more SpO2 estimates using the one or more physiological signals. In accordance with a determination that a first set of criteria is satisfied, the processing circuitry can generate an alert (e.g., indicative of sustained low SpO2). In accordance with a determination that the first set of criteria is satisfied, the processing circuitry can forgo generating the alert. Additionally or alternatively to one or more of the examples disclosed above, in some examples, the first set of criteria can include a criterion that is satisfied when a first threshold number of the one or more SpO2 estimates fall below a first SpO2 estimate threshold: Additionally or alternatively to one or more of the examples disclosed above, in some examples, the first set of criteria can include a criterion that is satisfied when the first threshold number of the one or more SpO2 estimates that fall below a first SpO2 estimate threshold occur across over a threshold time period (e.g., over an hour, two hours, 6 hours, etc.). Additionally or alternatively to one or more of the examples disclosed above, in some examples, the first set of criteria can include a criterion that is satisfied when the first threshold number of the one or more SpO2 estimates that fall below a first SpO2 estimate threshold occur without an intervening SpO2 estimate above a second threshold.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A wearable device comprising:
an optical sensor including a plurality of channels and configured to measure physiological signals from the plurality of channels; and
a processor coupled to the optical sensor and programmed to:
in accordance with a determination that two or more first criteria are satisfied, the two or more first criteria including a motion criterion that is satisfied when a measure of motion is less than a motion threshold and a timing criteria including a first timing criterion that is satisfied when a threshold period of time has passed since a prior measurement of the physiological signals of threshold quality and without termination, by the optical sensor to compute a prior SpO2 estimate:
measure first physiological signals using the optical sensor; and
process the first physiological signals to compute an SpO2 estimate using the first physiological signals.

2. The wearable device of claim 1, wherein the processor is further programmed to:
in accordance with a determination that two or more first criteria are not satisfied:
forgo measuring the first physiological signals; and
forgo processing the first physiological signals to compute the SpO2 estimate.

3. The wearable device of claim 1, wherein the two or more first criteria include a posture criterion that is satisfied when predetermined postures are excluded based on motion data.

4. The wearable device of claim 1, wherein the two or more first criteria include an on-wrist criterion that is satisfied when the optical sensor is detected in proximity to or contact with a user's tissue.

5. The wearable device of claim 4, wherein the two or more first criteria include a settling time criterion that is satisfied a second threshold period of time after satisfying the on-wrist criterion.

6. The wearable device of claim 1, wherein the timing criteria further include a second timing criterion that is satisfied when fewer than a threshold number of prior measurement of the physiological signals by the optical sensor have been performing within a second threshold period of time.

7. The wearable device of claim 1, wherein measuring the first physiological signals using the optical sensor includes measuring data for a plurality of windows, including a first window of first data from the plurality of channels, a second window of second data from the plurality of channels.

8. The wearable device of claim 7, wherein the first window and the second window partially overlap.

9. The wearable device of claim 7, wherein processing the first physiological signals to compute the SpO2 estimate using the first physiological signals comprises:

computing a plurality of window SpO2 estimates, each of the plurality of window SpO2 estimates computed using the data corresponding to one of the plurality of windows; and computing the SpO2 estimate using the plurality of window SpO2 estimates.

10. The wearable device of claim 1, the processor further programmed to:

in accordance with a determination that one or more second criteria are satisfied, the second criteria including a motion criterion that is satisfied when the measure of motion is greater than a threshold for a second threshold period of time after measuring the first physiological signals:

measure second physiological signals using the optical sensor; and process the second physiological signals to compute a second SpO2 estimate using the second physiological signals.

11. The wearable device of claim 1, wherein the processor is programmed to measure and process the first physiological signals without user intervention.

12. The wearable device of claim 1, wherein the processor is further programmed to:

in accordance with a determination that one or more termination criteria are satisfied while measuring the first physiological signals using the optical sensor, cease measuring the first physiological signals; and in accordance with a determination that one or more termination criteria are not satisfied while measuring the first physiological signals using the optical sensor, continue measuring at least a portion of the first physiological signals.

13. The wearable device of claim 12, wherein the termination criteria include a motion criterion that is satisfied when the measure of motion is greater than the motion threshold.

14. The wearable device of claim 12, wherein the termination criteria include a motion criterion that is satisfied when the measure of motion is greater than the motion threshold for at least a portion of each window of the first physiological signals.

15. The wearable device of claim 12, wherein the processor is further programmed to:

in accordance with a determination that one or more termination criteria are satisfied while measuring the first physiological signals using the optical sensor:

in accordance with a determination that the first physiological signals measured before ceasing measuring the first physiological signals includes more than a threshold amount of data, compute the SpO2 estimate; and in accordance with a determination that the first physiological signals measured before ceasing measuring the first physiological signals includes less than the threshold amount of data, forgo computing the SpO2 estimate.

16. A method comprising:

in accordance with a determination that two or more first criteria are satisfied, the two or more first criteria including a motion criterion that is satisfied when a measure of motion is less than a motion threshold and a timing criteria including a first timing criterion that is satisfied when a threshold period of time has passed since a prior measurement of physiological signals of threshold quality and without termination, by an optical sensor to compute a prior SpO2 estimate:

measuring first physiological signals using the optical sensor including a plurality of channels and configured to measure physiological signals from the plurality of channels; and processing the first physiological signals to compute an SpO2 estimate using the first physiological signals.

17. The method of claim 16, further comprising:

in accordance with a determination that two or more first criteria are not satisfied:

forgoing measuring the first physiological signals; and forgoing processing the first physiological signals to compute the SpO2 estimate.

18. The method of claim 16, wherein the two or more first criteria include a posture criterion that is satisfied when predetermined postures are excluded based on motion data.

19. A non-transitory computer readable storage medium storing instructions, which when executed by an electronic device including processing circuitry, cause the processing circuitry to:

in accordance with a determination that two or more first criteria are satisfied, the two or more first criteria including a motion criterion that is satisfied when a measure of motion is less than a motion threshold and a timing criteria including a first timing criterion that is satisfied when a threshold period of time has passed since a prior measurement of physiological signals of threshold quality and without termination, by an optical sensor to compute a prior SpO2 estimate:

measure first physiological signals using the optical sensor including a plurality of channels and configured to measure physiological signals from the plurality of channels; and process the first physiological signals to compute an SpO2 estimate using the first physiological signals.

* * * * *